United States Patent
Lv et al.

(10) Patent No.: US 12,030,954 B2
(45) Date of Patent: Jul. 9, 2024

(54) ANTIBODY BINDING TO AXL PROTEIN AND APPLICATION THEREOF

(71) Applicants: HANGZHOU SUMGEN BIOTECH CO., LTD., Zhejiang (CN); SUMGEN MAB (BEIJING) BIOTECH CO., LTD., Beijing (CN)

(72) Inventors: Ming Lv, Zhejiang (CN); Xiaoran Ding, Zhejiang (CN); Shiwei Miao, Zhejiang (CN); Bin Tan, Zhejiang (CN); Xuegong Wang, Zhejiang (CN)

(73) Assignees: HANGZHOU SUMGEN BIOTECH CO., LTD., Zhejiang (CN); SUMGEN MAB (BEIJING) BIOTECH CO., LTD., Beijing (CN)

( * ) Notice: Subject to any disclaimer, the term of this patent is extended or adjusted under 35 U.S.C. 154(b) by 842 days.

(21) Appl. No.: 17/059,019

(22) PCT Filed: May 28, 2019

(86) PCT No.: PCT/CN2019/088794
§ 371 (c)(1),
(2) Date: Nov. 25, 2020

(87) PCT Pub. No.: WO2019/228345
PCT Pub. Date: Dec. 5, 2019

(65) Prior Publication Data
US 2021/0230295 A1    Jul. 29, 2021

(30) Foreign Application Priority Data

May 29, 2018   (CN) .......................... 201810528095.2

(51) Int. Cl.
| C07K 16/30 | (2006.01) |
| A61K 39/00 | (2006.01) |
| A61K 47/68 | (2017.01) |
| A61P 35/00 | (2006.01) |
| C07K 16/40 | (2006.01) |

(52) U.S. Cl.
CPC .......... *C07K 16/30* (2013.01); *A61K 47/6851* (2017.08); *A61P 35/00* (2018.01); *C07K 16/40* (2013.01); *A61K 2039/505* (2013.01)

(58) Field of Classification Search
CPC .... C07K 16/30; C07K 16/40; C07K 2317/24; C07K 2317/565; C07K 2317/77; C07K 2317/92; C07K 16/2863; A61K 47/6851; A61K 2039/505; A61K 47/6849; A61K 47/6877; A61K 47/6803; A61P 35/00
See application file for complete search history.

(56) References Cited

U.S. PATENT DOCUMENTS

| 2015/0152193 A1* | 6/2015 | Hettmann ........ G01N 33/57415 |
| | | 435/69.6 |
| 2021/0317230 A1* | 10/2021 | Lv .......................... C07K 16/30 |
| 2022/0411531 A1* | 12/2022 | Lv .......................... G01N 33/68 |

FOREIGN PATENT DOCUMENTS

| CN | 102421802 A | 4/2012 | |
| CN | 103998468 A | 8/2014 | |
| CN | 107531786 A | 1/2018 | |
| CN | 107987163 A | 5/2018 | |
| WO | WO-2015193430 A1 * | 12/2015 | ....... A61K 39/39558 |
| WO | 2017009258 A1 | 1/2017 | |
| WO | 2017180842 A1 | 10/2017 | |

OTHER PUBLICATIONS

Tzartos, et al., Methods in Molecular Biology 1996, vol. 66 Epitope Mapping Protocols; Edited by GE Morns Humana Press, Inc. Totowa, NJ, pp. 55-66 (Year: 1996).*
Almagro & Fransson, Frontiers in Bioscience 2008; 13:1619-33 (Year: 2008).*
Marchalonis et al., Dev & Comp Immunol 30:223-247 (2006) (Year: 2006).*
Edwards et al, J Mol Biol 334:103-118 (2003) (Year: 2003).*
Shah, et al.,World J Clin Oncol Aug. 10, 2014; 5(3): 283-298 (Year: 2014).*
Cuzick, et al Lancet Oncol Jan. 2015; 16(1) (Year: 2015).*
Gjedrum, et al., PNAS 2010 107:1124 (Year: 2010).*
Zhu, et al., Molecular Cancer 2019 18:153 (Year: 2019).*
Chan, et al., PLoS ONE 2015 10(4) Article ID e0124708 (Year: 2015).*
PCT/CN2019/088794 International Search Report dated Aug. 27, 2019.

* cited by examiner

*Primary Examiner* — Julie Wu
*Assistant Examiner* — John L Van Druff
(74) *Attorney, Agent, or Firm* — Honigman LLP; Thomas A. Wootton, Esq.; Jonathan P. O'Brien

(57) ABSTRACT

Provided is an antibody or an antigen-binding fragment thereof, having one or more properties selected from the group consisting of: 1) being capable of binding to an AXL protein by a $K_D$ value of $1 \times 10^{-8}$ M or lower; 2) being capable of specifically recognizing an AXL protein expressed on a cell surface; and 3) being capable of mediating internalization after binding to the AXL protein expressed on the cell surface. The antibody may further used for constructing an immunoconjugate. The antibody and the immunoconjugate may inhibit the proliferation of tumor cells.

14 Claims, 6 Drawing Sheets
Specification includes a Sequence Listing.

ANTIBODY BINDING TO AXL PROTEIN AND APPLICATION THEREOF

CROSS-REFERENCE TO RELATED APPLICATIONS

This application is a National Stage Application and claims priority under 35 U.S.C. § 371 to Patent Cooperation Treaty application PCT/CN2019/088794, filed May 28, 2019, which claims the benefit of CN 201810528095.2 filed May 29, 2018. Priority is claimed to these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "2020-11-24_262790-480663_ST25.txt" is 29,571 bytes in size and was created on Nov. 24, 2020, 2020, and filed electronically herewith.

TECHNICAL FIELD

The present application relates to an antibody binding to an AXL protein and use thereof. The antibody can specifically recognize and bind to the AXL protein, and mediate the internalization after binding to the AXL protein expressed on the cell surface. The antibody can inhibit the growth and/or proliferation of tumors or tumor cells.

BACKGROUND ART

AXL (a receptor tyrosine kinase) is a member of the kinase Tyro-3 family, which can be activated by binding to the ligand Gas6 (a 70-kDa protein homologous to the anticoagulant factor protein S). The activation of AXL results in a signal transduction via a PI-3-kinase/Akt (Franke et al., Oncogene 22: 8983-8998, 2003) and other primary pathways, e.g., Ras/Erk and β-catenin/TCF (Goruppi et al., Mol. Cell Biol. 21: 902-915, 2001).

In tumor cells, AXL plays an important role in regulation of cell invasion and migration. The overexpression of AXL is associated not only with poor prognosis, but also with increased invasion of various human cancers reported in terms of breast, colon, esophageal cancer, liver cells, stomach, glioma, lung, melanoma, osteosarcoma, ovary, prostate, rhabdomyosarcoma, kidney, thyroid, and endometrial cancer (Linger R. M. Adv. Cancer Res. 2008, 100, 35-83 and Verma A. Mol. Cancer Ther. (2011). 10, 1763-1773).

Due to the therapeutic potential of AXL, there is a need of producing an antibody that specifically binds to the AXL protein.

SUMMARY OF THE INVENTION

The present application provides an antibody binding to the AXL protein and use thereof. The antibody or its antigen-binding fragment of the present application has one or more of the following properties: 1) binding to the AXL protein with a relatively high affinity and specificity; 2) specifically recognizing the AXL protein expressed on the cell surface; 3) mediating the internalization of the cell, especially the tumor cell, after binding to the AXL protein expressed on the cell surface; 4) inhibiting the growth and/or proliferation of tumors or tumor cells; and 5) being used to construct an immunoconjugate, and the immunoconjugate can also inhibit the growth and/or proliferation of tumors or tumor cells. The present application further provides a preparation method and use of the antibody.

In an aspect, the present application provides an antibody or its antigen-binding fragment with one or more properties selected from the group consisting of: 1) an ability of binding to an AXL protein with a $K_D$ value of $1 \times 10^{-8}$ M or below; 2) an ability of specifically recognizing an AXL protein expressed on the surface of a cell; 3) an ability of mediating an internalization after binding to an AXL protein expressed on the surface of a cell.

In certain embodiments, the AXL protein is a human AXL protein. In certain embodiments, the AXL protein includes an extracellular domain. In certain embodiments, the extracellular domain includes an amino acid sequence as set forth in SEQ ID NO: 2.

In certain embodiments, the cell includes a tumor cell.

In certain embodiments, the tumor is an AXL positive tumor. In certain embodiments, the tumor is selected from the group consisting of lung cancer, skin cancer, renal cancer, pancreatic cancer, hematological tumor, breast cancer, ovarian cancer, lymphoma and myeloma. In certain embodiments, the tumor is selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma.

In certain embodiments, the cell includes a human cell. In certain embodiments, the cell is selected from the group consisting of human non-small cell lung cancer A549 cell, human cutaneous squamous cell carcinoma A431 cell, renal clear cell adenocarcinoma 786-0 cell, human pancreatic cancer MIA PaCa-2 cell, erythroleukemia K562 cell, acute T cell leukemia Jurkat cell, human breast cancer MCF-7 cell, human breast cancer MDA-MB-231 cell, human breast cancer MDA-MB-468 cell, human breast cancer SKBR3 cell, human ovarian cancer SKOV3 cell, lymphoma U-937 cell, lymphoma Raji cell, human myeloma U266 cell and human multiple myeloma RPMI8226 cell.

In certain embodiments, the antibody is selected from the group consisting of monoclonal antibody, single strand antibody, chimeric antibody, polyspecific antibody, humanized antibody and fully human antibody.

In certain embodiments, the antigen-binding fragment is selected from the group consisting of Fab, Fab', $F(ab)_2$, $F(ab')_2$, Fv and ScFv fragments.

In certain embodiments, the antibody or its antigen-binding fragment competes with a reference antibody to bind to the AXL protein, wherein the reference antibody includes a light chain variable region and a heavy chain variable region, the light chain variable region of the reference antibody includes LCDR1, LCDR2 and LCDR3, the LCDR1 includes an amino acid sequence as set forth in SEQ ID NO: 4; the LCDR2 includes an amino acid sequence as set forth in SEQ ID NO: 5; and the LCDR3 includes an amino acid sequence as set forth in SEQ ID NO: 6; and the heavy chain variable region of the reference antibody includes HCDR1, HCDR2 and HCDR3, the HCDR1 includes an amino acid sequence as set forth in SEQ ID NO: 7; the HCDR2 includes an amino acid sequence as set forth in SEQ ID NO: 8; and the HCDR3 includes an amino acid sequence as set forth in SEQ ID NO: 9.

In certain embodiments, the light chain variable region of the reference antibody includes an amino acid sequence as set forth in SEQ ID NO: 10, and the heavy chain variable region of the reference antibody includes an amino acid sequence as set forth in SEQ ID NO: 11. In certain embodiments, the light chain of the reference antibody includes an amino acid sequence as set forth in SEQ ID NO: 12; and the heavy chain of the reference antibody includes an amino acid sequence as set forth in SEQ ID NO: 13.

In certain embodiments, the reference antibody is selected from the group consisting of antibody 6G12 and antibody C6G12.

In certain embodiments, the antibody includes an antibody light chain or its fragment. In certain embodiments, the antibody light chain or its fragment includes LCDR1, and the LCDR1 includes an amino acid sequence as set forth in SEQ ID NO: 4. In certain embodiments, the antibody light chain or its fragment includes LCDR2, and the LCDR2 includes an amino acid sequence as set forth in SEQ ID NO: 5. In certain embodiments, the antibody light chain or its fragment includes LCDR3, and the LCDR3 includes an amino acid sequence as set forth in SEQ ID NO: 6.

In certain embodiments, the antibody light chain or its fragment includes a light chain variable region VL, and the light chain variable region VL includes an amino acid sequence as set forth in SEQ ID NO: 10.

In certain embodiments, the antibody light chain or its fragment further includes a human constant region. In certain embodiments, the human constant region includes a human Igκ constant region.

In certain embodiments, the antibody light chain or its fragment includes an amino acid sequence as set forth in SEQ ID NO: 12.

In certain embodiments, the antibody includes an antibody heavy chain or its fragment. In certain embodiments, the antibody heavy chain or its fragment includes HCDR1, and the HCDR1 includes an amino acid sequence as set forth in SEQ ID NO: 7. In certain embodiments, the antibody heavy chain or its fragment includes HCDR2, and the HCDR2 includes an amino acid sequence as set forth in SEQ ID NO: 8. In certain embodiments, the antibody heavy chain or its fragment includes HCDR3, and the HCDR3 includes an amino acid sequence as set forth in SEQ ID NO: 9.

In certain embodiments, the antibody heavy chain or its fragment includes a heavy chain variable region VH, and the heavy chain variable region VH includes an amino acid sequence as set forth in SEQ ID NO: 11.

In certain embodiments, the antibody heavy chain or its fragment further includes a human constant region. In certain embodiments, the human constant region includes a human IgG constant region. In certain embodiments, the IgG constant region includes a human IgG1 constant region.

In certain embodiments, the antibody heavy chain or its fragment includes an amino acid sequence as set forth in SEQ ID NO: 13.

In certain embodiments, the antibody is selected from the group consisting of antibody 6G12 and antibody C6G12.

In another aspect, the present application provides one or more isolated nucleic acid molecules encoding the antibody or its antigen-binding fragment.

In another aspect, the present application provides one or more vectors including the nucleic acid molecule.

In another aspect, the present application provides a cell including the nucleic acid molecule or the vector.

In another aspect, the present application provides a method of preparing the antibody or its antigen-binding fragment, including culturing the cell under conditions that allow the antibody or its antigen-binding fragment to be expressed.

In another aspect, the present application provides an immunoconjugate including the antibody or its antigen-binding fragment.

In certain embodiments, the immunoconjugate further includes at least one additional agent selected from the group consisting of chemotherapeutic agents, radioactive elements, cell growth inhibitors and cytotoxic agents. In certain embodiments, the antibody or its antigen-binding fragment and the at least one additional agent in the immunoconjugate are linked via a joint molecule. In certain embodiments, the antibody or its antigen-binding fragment and the at least one additional agent in the immunoconjugate are covalently linked to the joint molecule, respectively.

In certain embodiments, the at least one additional agent includes maytansine or its derivative. In certain embodiments, the maytansine derivative includes maytansine derivative DM1.

In another aspect, the present application provides a pharmaceutical composition, including the antibody or its antigen-binding fragment, the immunoconjugate or the cell, and optionally pharmaceutically acceptable adjuvants.

In another aspect, the present application provides use of the antibody or its antigen-binding fragment or the immunoconjugate in preparation of a drug for preventing or treating tumors.

In certain embodiments, the tumor includes an AXL positive tumor. In certain embodiments, the tumor includes a tumor selected from the group consisting of lung cancer, skin cancer, renal cancer, pancreatic cancer, hematological tumor, breast cancer, ovarian cancer, lymphoma and myeloma. In certain embodiments, the tumor includes a tumor selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma.

In another aspect, the present application provides use of the antibody or its antigen-binding fragment or the immunoconjugate for preventing or treating tumors.

In certain embodiments, the tumor includes an AXL positive tumor. In certain embodiments, the tumor includes a tumor selected from the group consisting of lung cancer, skin cancer, renal cancer, pancreatic cancer, hematological tumor, breast cancer, ovarian cancer, lymphoma and myeloma. In certain embodiments, the tumor includes a tumor selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma.

In another aspect, the present application provides a method of preventing or treating a subject in need thereof, including administering to the subject the antibody or its antigen-binding fragment, the immunoconjugate or the pharmaceutical composition.

In certain embodiments, the tumor includes an AXL positive tumor. In certain embodiments, the tumor includes a tumor selected from the group consisting of lung cancer, skin cancer, renal cancer, pancreatic cancer, hematological tumor, breast cancer, ovarian cancer, lymphoma and myeloma. In certain embodiments, the tumor includes a tumor selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma.

In another aspect, the present application provides the antibody or its antigen-binding fragment for diagnosis of a disease or condition associated with the expression of the AXL protein.

In another aspect, the present application provides use of the antibody or its antigen-binding fragment in preparation of a diagnostic agent, wherein the diagnostic agent is used to diagnose a disease or condition associated with the expression of the AXL protein.

In another aspect, the present application provides a method of diagnosing a disease or condition associated with the expression of the AXL protein in a subject, including: contacting a sample derived from the subject with the antibody or its antigen-binding fragment and determining the presence and/or amount of a substance that can specifically bind to the antibody or its antigen-binding fragment.

Those skilled in the art can easily perceive of other aspects and advantages of the present disclosure from the detailed description below. The detailed description below only shows and describes the exemplary embodiments of the present disclosure. As those skilled in the art will recognize, the present disclosure enables those skilled in the art to make modifications to the disclosed embodiments without departing from the spirit and scope of the invention involved by the present application. Correspondingly, the drawings and description of the present specification are only exemplary, rather than restrictive.

BRIEF DESCRIPTION OF THE DRAWINGS

The specific features of the invention involved by the present application are shown in the appended claims. By referring to the exemplary embodiments described in detail below and the accompanying drawings, the features and advantages of the invention involved by the present application can be better understood. The drawings are briefly described as follows.

DETAILED DESCRIPTION OF THE EMBODIMENTS

Figure 1:
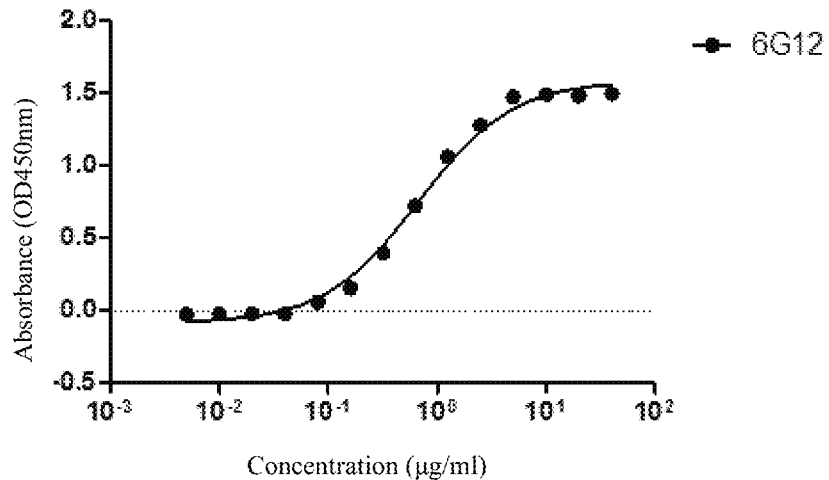
FIG. 1 shows the binding ability of the monoclonal antibody of the present application specifically binding to AXL-Fc.

Hereinafter embodiments of the invention involved by the present application are illustrated by specific examples, and persons skilled in the art can readily understand other advantages and effects of the invention involved by the present application from the disclosure of the present specification.

In the present application, the term "antibody" refers generally to a polypeptide molecule capable of specifically recognizing and/or neutralizing a specific antigen. For example, the antibody can include a heavy (H) chain and/or a light (L) chain (e.g., it can be an immunoglobulin that can include two heavy chains and/or light chains), and include any molecule including its antigen-binding fragment. The term "antibody" can include monoclonal antibody, antibody fragments or antibody derivative, including but not limited to human antibody (fully human antibody), humanized antibody, chimeric antibody, single strand antibody (e.g., scFv), and antigen-binding fragment (e.g., Fab, Fab' and (Fab)₂ fragments). Each heavy chain can be composed of heavy chain variable regions (VHs) and heavy chain constant regions. Each light chain can be composed of light chain variable regions (VLs) and light chain constant regions. VH and VL regions can be further divided into hypervariable regions called complementary determining regions (CDRs), which are dispersed in more conserved regions called framework regions (FRs). Each of VH and VL can be composed of three CDRs and four FR regions, which can be arranged from the amino terminus to the carboxyl terminus in the order of FR1, CDR1, FR2, CDR2, FR3, CDR3 and FR4. The variable regions of heavy chain and light chain include binding domains that interact with the antigen. The constant regions of the antibody can mediate the binding of the immunoglobulin to the host tissues or factors.

In the present application, the term "antigen-binding fragment" refers generally to one or more fragments in the antibody that function to specifically bind to the antigen. The antigen-binding function of the antibody can be achieved by a full length fragment of the antibody. And the antigen-binding function of the antibody can also be achieved by the following: a heavy chain including Fv, ScFv, dsFv, Fab, Fab' or F(ab')₂ fragments, or a light chain including Fv, ScFv, dsFv, Fab, Fab' or F(ab')₂ fragments. (1) Fab fragment, that is a monovalent fragment composed of VL, VH, CL and CH domains; (2) F(ab')₂ fragment, that is a divalent fragment including two Fab fragments linked via a disulfide bond in the hinge region; (3) Fd fragment composed of VH and CH domains; (4) Fv fragment composed of VL and VH domains of a single arm of the antibody; (5) dAb fragment composed of VH domains (Ward et al., (1989) Nature 341: 544-546); (6) isolated complementary determining regions (CDRs); and (7) a combination of two or more CDRs that are optionally linked via a linker. Moreover, it can also include a monovalent single-strand molecule Fv (scFV) formed by pairing of VL and VH (see, Bird et al., (1988) Science 242: 423-426; and Huston et al., (1988) Proc. Natl. Acad. Sci. 85: 5879-5883). The "antigen-binding portion" can further include a fusion protein including an immunoglobulin. For example, the fusion protein can include a binding domain selected from the group consisting of: (1) a binding domain polypeptide fused with the immunoglobulin hinge region polypeptide; (2) an immunoglobulin heavy chain CH2 constant region fused with the hinge region; and/or (3) an immunoglobulin heavy chain CH3 constant region fused with the CH2 constant region.

In the present application, the term "AXL protein" refers generally to protein receptor tyrosine kinase encoded by the axl gene. AXL (Ark, UFO, Tyro-7) is a member of the kinase Tyro-3 family that can be activated by the binding to a ligand Gas6 (a 70-kDa protein homogenous to the anticoagulant factor protein S). In some cancer (e.g., lung cancer, skin cancer, renal cancer, pancreatic cancer, hematological tumor, breast cancer, ovarian cancer, lymphoma or myeloma) cells, there may be overexpression of the AXL protein. The human AXL protein is a protein having 894 amino acids that can have an amino acid sequence as set forth in SEQ ID NO: 1; wherein the amino acid residues at positions 1-25 are the signal peptide; and the amino acid residues at positions of 26-442 are the extracellular domain of the AXL protein (that has an amino acid sequence as set forth in SEQ ID NO: 2).

In the present application, the term "an extracellular domain" refers generally to a polypeptide or protein domain located outside the cell. For example, the extracellular domain can be the extracellular domain of the AXL protein that has an amino acid sequence as set forth in SEQ ID NO: 2. The extracellular domain of the AXL protein can have a structure required by accessing a cell adhesion molecule. The extracellular domain of the AXL protein can be a combination of two immunoglobulin-like domains, and can bind to a Gas6 ligand (Sasaki T et al., EMBO J. (2006). 25, 80-87).

In the present application, the term "$K_D$" can be interchangeably used with "KD", and refers generally to the dissociation equilibrium constant of a specific antibody-antigen interaction at a unit of M(mol/L). KD can be calculated by the concentrations of material AB, as well as material A and material B dissociated therefrom: KD=c (A)*c (B)/c (AB). It can be seen from the equation that the greater the KD value, the more the dissociation, indicating that the weaker the affinity of materials A and B; otherwise, the smaller the KD value, the less the dissociation, indicating that the stronger the affinity of materials A and B.

In the present application, the term "internalization" generally refers to a process that the antibody or its antigen-binding fragment or polypeptide specifically binds to the receptor on the cell surface, forms a receptor-antibody complex, and then enters into the cell through endocytosis mediated by this receptor. At that time, such antibody or its antigen-binding fragment (e.g., Fab fragment) can become an internalized antibody. The internalized antibody can serve as a vector for targeted delivery of drugs, enzymes, or DNAs. In certain cases, the internalization can inhibit the proliferation of tumor cells. For example, the internalized antibody can be used to couple anti-tumor chemotherapeutics, radioactive elements, cell growth inhibitors and cytotoxic agents, and used as a candidate molecule for tumor biotherapy.

In the present application, the term "tumor" refers generally to a physiological condition characterized by dysregulation of cell proliferation or survival. The tumor can include all the known cancers and tumor conditions, no matter their characteristics are malignant, benign, soft tissue, or solids, and can include cancers of all stages and grades including pre-metastatic and post-metastatic cancers. The tumor can further include one or more tumor cells.

In the present application, the term "AXL positive tumor" refers generally to a tumor that is associated with the expression of the AXL protein, or has a significantly increased expression of the AXL protein. The AXL positive tumor can be selected from the group consisting of lung cancer, skin cancer, renal cancer, pancreatic cancer, hematological tumor, breast cancer, ovarian cancer, lymphoma and myeloma, or, the AXL positive tumor can be selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma. The AXL positive tumor can include one or more tumor cells. For example, the tumor cell can be selected from the group consisting of human non-small cell lung cancer A549 cell, human cutaneous squamous cell carcinoma A431 cell, renal clear cell adenocarcinoma 786-0 cell, human pancreatic cancer MIA PaCa-2 cell, erythroleukemia K562 cell, acute T cell leukemia Jurkat cell, human breast cancer MCF-7 cell, human breast cancer MDA-MB-231 cell, human breast cancer MDA-MB-468 cell, human breast cancer SKBR3 cell, human ovarian cancer SKOV3 cell, lymphoma U-937 cell, lymphoma Raji cell, human myeloma U266 cell and human multiple myeloma RPMI8226 cell.

In the present application, the term "monoclonal antibody" refers generally to a population of substantially homogeneous antibodies, that is, various antibodies contained in the population are the same except potential naturally occurring mutations present in a trace amount. The monoclonal antibody can be highly specific, and directly target a single antigenic site. The monoclonal antibody can be prepared by hybridoma technology or produced in bacteria, eukaryotic animals or plant cells by using recombinant DNA methods. The monoclonal antibody can also be obtained from a phage antibody library, by using a technology as described in, e.g., Clackson et al., Nature, 352:624-628 (1991) and Marks et al., Mol. Biol., 222:581-597 (1991).

In the present application, the term "single strand antibody" (scFv) refers generally to a molecule including antibody heavy chain variable regions and light chain variable regions. For example, the scFv can be formed by linking an antibody heavy chain variable region to a light chain variable region via a joint molecule (linker) (e.g., a connecting peptide).

In the present application, the term "chimeric antibody" refers generally to an antibody in which a part of the amino acid sequences of the heavy chain or the light chain is homogeneous to the corresponding amino acid sequence in an antibody derived from specific species or belongs to a certain class, while the other part of the chain is homogeneous to the corresponding sequence in another species. For example, the variable regions of the light chain and the heavy chain can be derived from the variable region of the antibody of an animal species (e.g., mice, rats, and the like), while the constant part is homogeneous to the sequence of an antibody derived from another species (e.g., human). For example, to obtain a chimeric antibody, the variable region can be produced by using non-human B cell or hybridoma cells, while the constant region combined therewith is derived from human. Since the constant region of the chimeric antibody can be derived from human, the chimeric antibody is less likely to elicit an immune response when injected than the antibody that uses a constant region of non-human origin.

In the present application, the term "humanized antibody" refers generally to an antibody that includes less sequence derived from non-human immunoglobulin, so as to reduce the immunogenicity when a heterogeneous antibody is introduced into a human. For example, it is feasible to use CDR transplant (Jones et al., Nature 321:522 (1986)) and its variant; including "reshaping" (Verhoeyen, et al., 1988 Science 239:1534-1536; Riechmann, et al., 1988 Nature 332: 323-337; Tempest, et al., Bio/Technol 1991 9:266-271), "hyperchimerization" (Queen, et al., 1989 Proc Natl Acad Sci USA 86:10029-10033; Co, et al., 1991 Proc Natl Acad Sci USA 88:2869-2873; Co, et al., 1992 J Immunol 148: 1149-1154) and "veneering" (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312), surface rendering (U.S. Pat. No. 5,639,641) and other technical means to humanize the binding domain of non-human source. If other regions, e.g., the hinge region and the constant region domain, are also derived from a non-human origin, these regions can also be humanized.

In the present application, the term "fully human antibody" refers generally to a full human antibody, namely, both the constant region and the variable regions of the antibody are derived from human. The fully human antibody can be achieved by phage antibody library technology, production of a humanized antibody by transgenic mice, ribosome display technology, EBV transformed B cell cloning technology, single B cell cloning and other technologies, and the like.

In the present application, the term "polyspecific antibody" refers generally to an antibody molecule capable of recognizing two or more antigens or epitopes. The polyspecific antibody can be obtained in a eukaryotic expression system or in a prokaryotic expression system by chemical coupling method, hybrid-hybridoma method, genetic engineering antibody preparation method and other methods.

In the present application, the term "immunoconjugate" refers generally to a conjugate formed by the conjugation of additional agents (e.g., chemotherapeutic agents, radioactive elements, cell growth inhibitors and cytotoxic agents) with the antibody or its antigen-binding fragment (e.g., covalently linked via a joint molecule), and the conjugate can deliver the additional agents to the target cell (e.g., tumor cells) by the specific binding of the antibody or its antigen-binding fragment to the antigen on the target cell. Then, the immunoconjugate undergoes internalization, and finally enters into the target cells (e.g., into vesicles like lysosome, etc.), and at that time the joint molecule in the immunoconjugate can be split to release the additional agents, thereby exerting its cytotoxic effect. Moreover, the antigen can also be secreted by the target cells, and located in a gap outside the target cells.

In the present application, the term "chemotherapeutic agents" refers generally to an agent for chemotherapy that can inhibit the proliferation of tumors and/or tumor cells. The chemotherapeutic agent may be selected from the group consisting of mitotic inhibitors, kinase inhibitors, alkylating agents, antimetabolites, embedded antibiotics, growth factor inhibitors, cell cycle inhibitors, enzymes, topoisomerase inhibitors, group protein deacetylase inhibitors, anti-survival agents, biological response modifiers, anti-hormones such as anti-androgens and anti-angiogenic agents. For example, the chemotherapeutic agent may be selected from the group consisting of capecitabine, daunorubicin, daunorubicin, actinomycin D, doxorubicin, epirubicin, idarubicin, isorubicin Bicing, bleomycin, mafosfamide, ifosfamide, cytarabine, dichloroethylnitrosourea, busulfan, mitomycin C, actinomycin D, plicamycin, prednisone, hydroxyprogesterone, testosterone, tamoxifen, dacarbazine, procarbazine, hexamethylmelamine, pentamethylmelamine, mitoxantrone, amsacrine, chlorambucil, methyl cyclohexylnitrosourea, nitrogen mustard, melphalan, cyclophosphamide, 6-mercaptopurine, 6-thioguanine, cytarabine (CA), 5-azacytidine, hydroxyurea, pentostatin, 4-hydroxyperoxycyclophosphamide, 5-fluorouracil (5-FU), 5-fluorodeoxyuridine (5-FUdR), methotrexate (MTX), colchicine, taxol (taxol), vincristine, vinblastine, etoposide, trimetrexate, teniposide and/or diethylstilbestrol (DES).

In the present application, the term "radioactive elements" refers generally to an element for radiotherapy that can inhibit the proliferation of tumors and/or tumor cells. The radioactive elements can be selected from the group consisting of $^3$H, $^{14}$C, $^{15}$N, $^{35}$S, $^{90}$Y, $^{99}$Tc, $^{111}$In, $^{125}$I and/or $^{131}$I.

In the present application, the term "cell growth inhibitor" generally refers to an agent that inhibits tumors by inhibiting growth factors that promote tumor cell growth and replication. The growth factors bind to the receptors on the cell surface to activate the intracellular signaling pathways. Complicated pathways may promote uncontrolled cell growth, leading to excessive cell division and developing into tumors. The cell growth inhibitor can inhibit the effects of these growth factors. The cell growth inhibitor can be selected from the group consisting of angiogenesis inhibitor, deacetylase (HDAC) inhibitor, Hedgehog signaling pathway blocker, mTOR inhibitor, p53/mdm2 inhibitor, PARP inhibitor, proteasome inhibitors and/or tyrosine kinase inhibitors.

In the present application, the term "cytotoxic agent" generally refers to an agent that inhibits the proliferation of tumors and/or tumor cells by producing toxins on the acting cells. The cytotoxic agent can be selected from the group consisting of alkylating agents such as, busulfan, hexamethylmelamine, thiotepa, cyclophosphamide, chlorambucil, uramustine, melphalan, chlorambucil, carmustine, streptozotocin, dacarbazine, temozolomide, ifosfamide, etc.; antitumor agents, e.g., mitomycin C, etc.; antimetabolites, e.g., methotrexate, azathioprine, mercaptopurine, fludarabine, 5-fluorouracil, etc.; platinum-containing anticancer agents, e.g., cisplatin, carboplatin, etc.; anthracyclines, e.g., daunorubicin, doxorubicin, epirubicin, idarubicin, mitoxantrone, etc.; plant alkaloids and terpenoids, e.g., vincristine, vinblastine, vinorelbine, vindesine, podophyllotoxin, docetaxel, etc.; topoisomerase inhibitors, e.g., irinotecan, amsacrine, topotecan, etoposide, teniposide, etc.; antibodies, e.g., rituximab, trastuzumab, bevacizumab, erlotinib, dactinomycin, finasteride; aromatase inhibitor; tamoxifen; goserelin; paclitaxel and/or imatinib mesylate. The cytotoxic agent can be administered by oral administration, injection, and the like.

In the present application, the term "joint molecule" refers generally to a functional molecule linking or connecting two molecules. For example, the joint molecule can link one molecule to another molecule (e.g., one molecule is a protein molecule, and another molecule is also a protein molecule, or can be a small molecular drug). The joint molecule can be used in the construction of the immunoconjugate. In the immunoconjugate, the joint molecule can have two functional characteristics: 1) The immunoconjugate is stable in circulating system, that is, the immunoconjugate cannot be split to release the additional agents in the circulating system until it reaches the target cell, thereby avoiding the production of toxic effect. 2. The joint molecule is required to be rapidly and effectively split once it enters into the target cell, so that the additional agents are effectively released to produce its due pharmacological activity. The joint molecule can be composed of polar or nonpolar amino acids. The joint molecule can also be a carbon chain including heteroatoms(s) (e.g., nitrogen atoms, sulfur atoms, and the like). The length of the joint molecule can be between 2 and 100 atoms, e.g., between 2 and 50 atoms, and can also be 3, 5, 10, 15, 20, 25, 30, 35, 40, 45 or 50 atoms; alternatively, e.g., the length of the linker can be 20 to 26 (20, 21, 22, 23, 24, 25 or 26) atoms. The joint molecule can be substituted by a substituent selected from the group consisting of hydrogen atoms, alkyl, alkenyl, alkynyl, amino, alkylamino, dialkylamino, trialkylamino, hydroxyl, alkoxy, halogen, aryl, heterocyclyl, heteroaryl, cyano, amide, carbamoyl, carboxylic acid, ester, thioether, alkylthioether, thiol, and ureido. Moreover, the joint molecule can be selected from the group consisting of pH-sensitive joint molecule, proteinase-cleavable joint molecule, nuclease-sensitive joint molecule, lipase-sensitive joint molecule, glycosidase joint molecule, hypoxic joint molecule, photocleavable joint molecule, thermally unstable joint molecule and ultrasound-sensitive joint molecule.

In the present application, the term "covalent/covalently" refers generally to a covalent bond, that is, two or more atoms share a pair of electrons and reach a state of electron saturation to form a relatively stable chemical structure. The formation of covalent bond involves the pairing of electrons with opposite spin directions between two adjacent atoms. At this time, the atomic orbits overlap with each other, and the electron cloud density between the two nuclei increases relatively, thereby increasing the attraction to the two nuclei. Covalent bonds can have saturation and directionality. Covalent bonds can be divided into non-polar covalent bonds, polar covalent bonds and coordination bonds. Compounds containing only covalent bonds can be called covalent compounds.

In the present application, the term "maytansine" refers generally to a compound isolated from *Maytenus molina* plants (see, U.S. Pat. No. 3,896,111), which belongs to antimitotic cytotoxins and has a structural formula as follows:

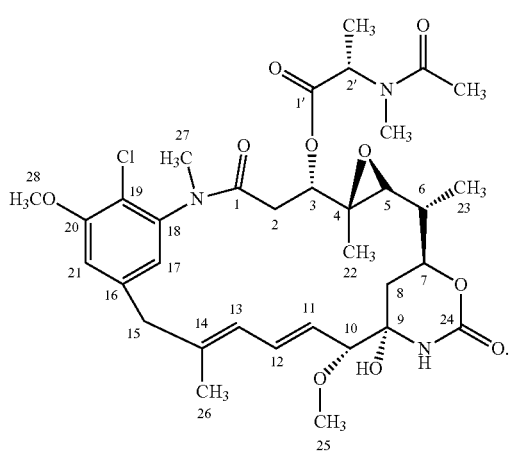

The CAS number of maytansine is 35846-53-8. Maytansine can produce a significant therapeutic effect on various tumors, e.g., L-1210, P-388 leukemia, S-180, W-256, Lewis lung cancer and external nasopharyngeal carcinoma. The maytansine derivative can include compounds that have the ring structure of maytansine and one or more substituent modifications on the ring thereof, e.g., maytansine derivative DM1, DM4.

In the present application, the term "maytansine derivative DM1" refers generally to a compound with the following structural formula:

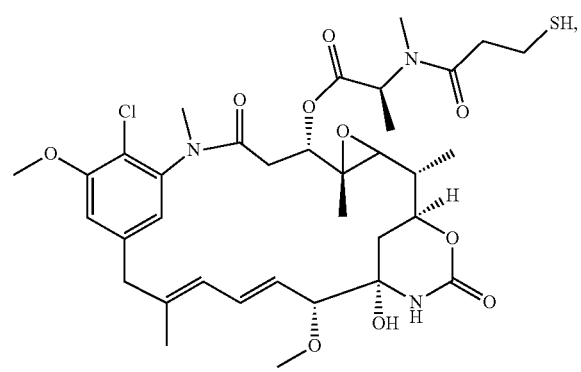 [SMILES: COc1cc2cc(c1Cl)N(C)C(=O)C[C@H](OC(=O)[C@H](C)N(C)C(=O)CCS)[C@]1(C)OC1[C@H](C)[C@@H]1C[C@@](O)(NC(=O)O1)[C@H](OC)/C=C/C=C(\C)C2]

of which the CAS number is 139504-50-0. The maytansine derivative DM1 can be an antimitotic cytotoxin.

In the present application, the term "disease or condition associated with the expression of the AXL protein" refers generally to a disease or condition associated with the expression of the AXL protein, or caused by the upregulated expression of the AXL protein. The disease or condition can be selected from the group consisting of Zika virus infection, systemic lupus erythematosus, elevation of blood pressure, proteinuria, thyroid cancer, stomach cancer, lung cancer, skin cancer, renal cancer, pancreatic cancer, hematological tumor (e.g., acute myeloblastic leukemia), breast cancer (e.g., ER positive breast cancer), ovarian cancer (e.g., Type I and Type II epithelial ovarian cancer), lymphoma and myeloma, or, can be selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma.

In the present application, the term "nucleic acid molecule" refers generally to isolated forms of nucleotides, deoxyribonucleotides, or ribonucleotides of any length that are isolated from their natural environment or artificially synthesized or their analogs.

In the present application, the term "vector" generally refers to a nucleic acid molecule capable of self-replication in a suitable host, which transfers the inserted nucleic acid molecule into the host cell and/or between the host cells. The vector can include a vector mainly used for inserting DNA or RNA into cells, a vector mainly used for replicating DNA or RNA, and a vector mainly used for expression of DNA or RNA transcription and/or translation. The vector further includes a vector with a variety of the above described functions. The vector can be a polynucleotide that can be transcribed and translated into a polypeptide when introduced into a suitable host cell. Generally, by culturing a suitable host cell containing the vector, the vector can produce the desired expression product.

In the present application, the term "cell" generally refers to an individual cell, cell line, or cell culture that can include or has included a plasmid or vector containing the nucleic acid molecule of the present application, or can express the antibody or its antigen-binding fragment of the present application. The host cell can include the progeny of a single host cell. Due to natural, accidental or deliberate mutations, the progeny cells may not be exactly the same as the original parent cells in terms of morphology or genome, as long as they can express the antibody or its antigen-binding fragment of the present application. The host cell can be obtained by transfecting cells in vitro with the vector of the present application. The host cell can be a prokaryotic cell (e.g., *Escherichia coli*) or a eukaryotic cell (e.g., yeast cells, e.g., COS cells, Chinese Hamster Ovary (CHO) cells, HeLa cells, HEK293 cells, COS-1 cells, NSO cells, or myeloma cells). In some embodiments, the host cell is a mammalian cell. For example, the mammalian cell can be a CHO-K1 cell. In the present application, the term "recombinant host cell" generally refers to a cell into which a recombinant expression vector is introduced. The recombinant host cell includes not only a certain specific cell, but also the progeny thereof.

In the present application, the term "about" refers generally to a variation within 0.5%-10% of the given value, e.g., a variation within 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the given value.

In the present application, the term "include" generally means comprise, contain, have, or include. In some cases, it also means "be" or "consist of".

Antibody, its Antibody-Binding Fragment or Variant

In an aspect, the present application provides an antibody or its antigen-binding fragment or variant that binds to the AXL protein with a KD value of $1\times10^{-8}$ M or below (e.g., the KD value is not greater than about $1\times10^{-8}$ M, not greater than about $1\times10^{-9}$ M, not greater than about $5\times10^{-10}$ M, not greater than about $4\times10^{-10}$ M, not greater than about $3\times10^{-10}$ M, not greater than about $2\times10^{-10}$ M, not greater than $1.6\times10^{-10}$ M, not greater than $1.5\times10^{-10}$ M, not greater than $1.4\times10^{-10}$ M, not greater than $1.3\times10^{-10}$ M, not greater than $1.2\times10^{-10}$ M, not greater than $1.1\times10^{-10}$ M, not greater than about $1\times10^{-10}$ M or not greater than about $1\times10^{-11}$ M or below).

The antibody or its antigen-binding fragment of the present application can specifically recognize the AXL protein expressed on the cell surface.

The antibody or its antigen-binding fragment of the present application can mediate the internalization after binding to an AXL protein expressed on the surface of cell. For example, the internalization can include the following steps: when the antibody or its antigen-binding fragment can bind to the plasma membrane of a cell (for example, a tumor cell), or can respond to the proteolytic activity in the cell microenvironment (for example, tumor cell microenvironment), it will be released in the cell, therefore the antibody or its antigen-binding fragment can be engulfed by the cell membrane and absorbed into the cell. In certain embodiments, the antibody or its antigen-binding fragment in the immunoconjugate and/or the additional agents conjugated therewith can also be engulfed by the cell membrane and absorbed into the cell after the antibody or its antigen-binding fragment binds to the plasma membrane of the cell.

In the present application, the AXL protein can be a human AXL protein (AAH32229.1); and can also be a *Macaca fascicularis* AXL protein (with the Genbank accession number of HB387229.1). For example, the AXL protein can be a human AXL protein with an amino acid sequence of SEQ ID NO: 1.

The AXL protein can include a variant of the AXL protein. For example, the variant can be: 1) a protein or polypeptide formed by substitution, deletion, or addition of one or more amino acids in the amino acid sequence of the AXL protein; and 2) a protein or polypeptide with at least about 85% (e.g., at least about 85%, about 90%, about 91%, about 92%, about 93%, about 94%, about 95%, about 96%, about 97%, about 98%, about 99% or higher) of sequence homology with the AXL protein.

The AXL protein can further include a fragment of the AXL protein. For example, the AXL protein can be an extracellular domain of a human AXL protein having an amino acid sequence as set forth in SEQ ID NO: 2.

In the present application, the cell can include a tumor cell. For example, the tumor can be an AXL positive tumor. For example, the tumor can be selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma.

In the present application, the cell can include a human cell. For example, the cell can include a cell selected from the group consisting of human non-small cell lung cancer A549 cell, human cutaneous squamous cell carcinoma A431 cell, renal clear cell adenocarcinoma 786-0 cell, human pancreatic cancer MIA PaCa-2 cell, erythroleukemia K562 cell, acute T cell leukemia Jurkat cell, human breast cancer MCF-7 cell, human breast cancer MDA-MB-231 cell, human breast cancer MDA-MB-468 cell, human breast cancer SKBR3 cell, human ovarian cancer SKOV3 cell, lymphoma U-937 cell, lymphoma Raji cell, human myeloma U266 cell and human multiple myeloma RPMI8226 cell.

The antibody of the present application can be selected from the group consisting of monoclonal antibody, single strand antibody, chimeric antibody, polyspecific antibody, humanized antibody and fully human antibody.

The antigen-binding fragment of the present application can be selected from the group consisting of Fab, Fab', F(ab)$_2$, Fv and ScFv fragments.

The antibody or its antigen-binding fragment of the present application can compete with a reference antibody to bind to the AXL protein. The reference antibody can include a light chain variable region and a heavy chain variable region. For example, the light chain variable region of the reference antibody can include LCDR1, LCDR2 and LCDR3, the LCDR1 includes an amino acid sequence as set forth in SEQ ID NO: 4; the LCDR2 includes an amino acid sequence as set forth in SEQ ID NO: 5; and the LCDR3 includes an amino acid sequence as set forth in SEQ ID NO: 6. The heavy chain variable region of the reference antibody can include HCDR1, HCDR2 and HCDR3, the HCDR1 includes an amino acid sequence as set forth in SEQ ID NO: 7; the HCDR2 includes an amino acid sequence as set forth in SEQ ID NO: 8; and the HCDR3 includes an amino acid sequence as set forth in SEQ ID NO: 9.

In the present application, the competitive binding capacity can be evaluated by determining the dissociation equilibrium constant of the antibody-antigen interaction of the antibody or its antigen-binding fragment. The method of detecting the dissociation equilibrium constant can be selected from the group consisting of ELISA, SRP, potentiometric titration, spectrophotometry, capillary electrophoresis, fluorometry and TLC pH method. For example, the antibody or its antigen-binding fragment can be detected by SRP (e.g., by use of biomacromolecular interaction instrument). By detection, it is found that the antibody of the present application, its antigen-binding fragment or variant can bind to the AXL protein with a KD value of $1\times10^{-8}$ M or below.

For example, the light chain variable region of the reference antibody can include an amino acid sequence as set forth in SEQ ID NO: 10, and the heavy chain variable region of the reference antibody can include an amino acid sequence as set forth in SEQ ID NO: 11. Alternatively, e.g., the amino acid sequence of the light chain of the reference antibody can include an amino acid sequence as set forth in SEQ ID NO: 12; and the heavy chain of the reference antibody can include an amino acid sequence as set forth in SEQ ID NO: 13.

For example, the antibody or its antigen-binding fragment of the present application can compete with a reference antibody to bind to the AXL protein. The reference antibody can include LCDR1-3 and HCDR1-3, and the LCDR1 can include an amino acid sequence as set forth in SEQ ID NO: 4; LCDR2 can include an amino acid sequence as set forth in SEQ ID NO: 5; and LCDR3 can include an amino acid sequence as set forth in SEQ ID NO: 6; and the HCDR1 can include an amino acid sequence as set forth in SEQ ID NO: 7; HCDR2 can include an amino acid sequence as set forth in SEQ ID NO: 8; and HCDR3 can include an amino acid sequence as set forth in SEQ ID NO: 9. In certain embodiments, the reference antibody can include antibodies 6G12, C6G12 or an antibody having the same LCDR1-3 and HCDR1-3 therewith. Alternatively, e.g., the reference antibody can include a light chain variable region and a heavy chain variable region, the amino acid sequence of the light chain variable region can include an amino acid sequence as set forth in SEQ ID NO: 10; and the heavy chain variable region can include an amino acid sequence as set forth in SEQ ID NO: 11. In certain embodiments, the antibody or its antigen-binding fragment can include antibodies 6G12, C6G12 or an antibody having the same light chain variable region and heavy chain variable region therewith. Alternatively, e.g., the reference antibody can include a light chain and a heavy chain, and the amino acid sequence of the light chain can include an amino acid sequence as set forth in SEQ ID NO: 12; and the amino acid sequence of the heavy chain can include an amino acid sequence as set forth in SEQ ID NO: 13. In certain embodiments, the antibody or its antigen-binding fragment can include the antibody C6G12 or antibody having the same light chain variable region and heavy chain variable region.

In the present application, the antibody or its antigen-binding fragment has a binding specificity. For example, the antibody or its antigen-binding fragment specifically recognizes the antigen—the AXL protein, but does not recognize other proteins. For example, the other proteins can be selected from the group consisting of a protein mixture derived from animals, immune cell surface antigen molecule CD family, tumor markers and TAM receptors, etc. For example, the other proteins can include: milk, BSA, CD19, TROP2, BCMA, CD47, CD38 and Gas6. In the present application, the binding specificity of the antibody or its antigen-binding fragment can be detected by ELISA. For example, the antibody or its antigen-binding fragment of the present application can have an absorbance OD value of more than 3 for the AXL protein at a wavelength of 450 nm, and an absorbance OD value below 0.5 for other proteins at the same wavelength.

The antibody or its antigen-binding fragment of the present application can include an antibody light chain or its fragment.

For example, the antibody light chain or its fragment can include LCDR1, and the LCDR1 can include an amino acid sequence as set forth in SEQ ID NO: 4. The antibody light chain or its fragment can include LCDR2, and the LCDR2 can include an amino acid sequence as set forth in SEQ ID NO:5. The antibody light chain or its fragment can include LCDR3, and the LCDR3 can include an amino acid sequence as set forth in SEQ ID NO: 6.

The light chain of the antibody of the present application or its fragments can include a light chain variable region VL, and the amino acid sequence of the light chain variable region VL can include an amino acid sequence as set forth in SEQ ID NO: 10.

For example, the antibody light chain or its fragment can include an Igκ constant region, e.g., a human Igκ constant region.

In certain embodiments, the amino acid sequence of the antibody light chain or its fragment can include an amino acid sequence as set forth in SEQ ID NO: 12.

The antibody or its antigen-binding fragment of the present application can include an antibody heavy chain or its fragment.

For example, the antibody heavy chain or its fragment can include HCDR1, and the HCDR1 can include an amino acid sequence as set forth in SEQ ID NO: 7. The antibody heavy chain or its fragment can include HCDR2, and the HCDR2 can include an amino acid sequence as set forth in SEQ ID NO: 8. Alternatively, e.g., the antibody heavy chain or its fragment can include HCDR3, and the HCDR3 can include an amino acid sequence as set forth in SEQ ID NO: 9.

The antibody heavy chain or its fragment can include a heavy chain variable region VH, and the heavy chain variable region VH can include an amino acid sequence as set forth in SEQ ID NO: 11.

For example, the antibody heavy chain or its fragment further includes a human constant region, wherein the human constant region can include a human IgG constant region. For example, the human IgG constant region can include a human IgG1 constant region.

In certain embodiments, the amino acid sequence of the antibody heavy chain can include an amino acid sequence as set forth in SEQ ID NO: 13.

In certain embodiments, the LCDR1 of the antibody or its antigen-binding fragment of the present application can include an amino acid sequence as set forth in SEQ ID NO: 4; LCDR2 can include an amino acid sequence as set forth in SEQ ID NO: 5; and LCDR3 can include an amino acid sequence as set forth in SEQ ID NO: 6; and HCDR1 can include an amino acid sequence as set forth in SEQ ID NO: 7; HCDR2 can include an amino acid sequence as set forth in SEQ ID NO: 8; and HCDR3 can include an amino acid sequence as set forth in SEQ ID NO: 9. For example, the antibody or its antigen-binding fragment can include the antibody 6G12 or an antibody having the same LCDR1-3 and HCDR 1-3 therewith. In certain embodiments, the light chain of the antibody or its antigen-binding fragment of the present application can include a light chain variable region, the light chain variable region can include an amino acid sequence as set forth in SEQ ID NO: 10; and the heavy chain can include a heavy chain variable region, the heavy chain variable region can include an amino acid sequence as set forth in SEQ ID NO: 11. For example, the antibody or its antigen-binding fragment can include an antibody 6G12 or an antibody having the same light chain variable region and heavy chain variable region therewith.

In certain embodiments, the antibody of the present application can be 6G12. The amino acid sequence of LCDR1-3 of the antibody 6G12 can be sequentially set forth in SEQ ID NO: 4, SEQ ID NO: 5 and SEQ ID NO: 6, and the amino acid sequence of HCDR1-3 can be sequentially set forth in SEQ ID NO: 7, SEQ ID NO: 8 and SEQ ID NO:

9; the amino acid sequence of VL can be set forth in SEQ ID NO: 10, and the amino acid sequence of VH can be set forth in SEQ ID NO: 11.

In certain embodiments, the amino acid sequence of LCDR1 of the antibody or its antigen-binding fragment of the present application can be set forth in SEQ ID NO: 4; the amino acid sequence of LCDR2 can be set forth in SEQ ID NO: 5; the amino acid sequence of LCDR3 can be set forth in SEQ ID NO: 6; and the amino acid sequence of HCDR1 can be set forth in SEQ ID NO: 7; the amino acid sequence of HCDR2 can be set forth in SEQ ID NO: 8; and the amino acid sequence of HCDR3 can be set forth in SEQ ID NO: 9. For example, the antibody or its antigen-binding fragment can include the antibody C6G12 or an antibody having the same LCDR1-3 and HCDR 1-3 therewith. In certain embodiments, the light chain of the antibody or its antigen-binding fragment of the present application can include a light chain variable region, the amino acid sequence of the light chain variable region can be set forth in SEQ ID NO: 10; and the heavy chain can include a heavy chain variable region, and the amino acid sequence of the heavy chain variable region can be set forth in SEQ ID NO: 11. For example, the antibody or its antigen-binding fragment can include the antibody C6G12 or an antibody having the same light chain variable region and heavy chain variable region. In certain embodiments, the antibody or its antigen-binding fragment of the present application can include a light chain and a heavy chain, the amino acid sequence of the light chain can be set forth in SEQ ID NO: 12 and the heavy chain amino acid sequence can be set forth in SEQ ID NO: 13. For example, the antibody or its antigen-binding fragment can include the antibody C6G12 or an antibody having the same light chain and heavy chain amino acid sequences.

In certain embodiments, the antibody of the present application can be C6G12. The amino acid sequence of LCDR1-3 of the antibody C6G12 can be sequentially set forth in SEQ ID NO: 4, SEQ ID NO:5 and SEQ ID NO: 6, and the amino acid sequence of HCDR1-3 can be sequentially set forth in SEQ ID NO: 7, SEQ ID NO: 8 and SEQ ID NO: 9; the amino acid sequence of VL can be set forth in SEQ ID NO: 10, and the amino acid sequence of VH can be set forth in SEQ ID NO: 11; and the amino acid sequence of the light chain can be set forth in SEQ ID NO: 12 and the amino acid sequence of the heavy chain can be set forth in SEQ ID NO: 13.

It should be understood that the protein, polypeptide and/or amino acid sequence involved in the present application include at least variants or homologs having the same or similar functions as the protein or polypeptide.

In the present application, the variant can be a protein or polypeptide formed by substitution, deletion or addition of one or more amino acids in the amino acid sequence of the protein and/or the polypeptide (e.g., the antibody or its antigen-binding fragment of the present application). For example, the variant can include a protein or polypeptide with changes of amino acids by substitution, deletion and/or insertion of at least 1, e.g., 1-30, 1-20 or 1-10, or e.g., 1, 2, 3, 4, or 5 amino acids. The functional variant can substantially maintain the biological characteristics of the protein or polypeptide before change (e.g., substitution, deletion or addition). For example, the functional variant can maintain at least 60%, 70%, 80%, 90%, or 100% of the biological activity (e.g., the ability of specifically binding to the AXL protein) of the protein or polypeptide before change.

In the present application, the homolog can be a protein or polypeptide having at least about 80% (e.g., at least about 85%, about 90%, about 91%, about 92%, about 93%, about 94%, about 95%, about 96%, about 97%, about 98%, about 99% or higher) of sequence homology with the amino acid sequence of the protein and/or the polypeptide (e.g., the antibody or its antigen-binding fragment of the present application).

In the present application, the homology refers generally to the degree of similarity or relevance among two or more sequences. The "percentage of sequence homology" can be calculated by the following way: the two sequences to be aligned are compared in a comparison window to determine the number of positions having the same nucleic acid bases (e.g., A, T, C, G, I) or the same amino acid residues (e.g., Ala, Pro, Ser, Thr, Gly, Val, Leu, Ile, Phe, Tyr, Trp, Lys, Arg, His, Asp, Glu, Asn, Gln, Cys and Met) in the two sequences to obtain the number of matching positions. The number of matching positions is divided by the total position number in the comparison window (i.e., the window size), and the result is multiplied by 100 to give the percentage of sequence homology. The alignment for determining the percentage of sequence homology can be performed in accordance with various methods known in the art, e.g., by use of publicly available computer softwares, e.g., BLAST, BLAST-2, ALIGN or Megalign (DNASTAR) softwares. Persons skilled in the art can determine appropriate parameters for the sequence alignment, including any algorithm required to achieve the maximum alignment within the full-length sequence being compared or within the target sequence region. The homology can also be determined by the following methods: FASTA and BLAST. For a description of the FASTA algorithm, see W. R. Pearson and D. J. Lipman's "Improved Tools for Biological Sequence Comparison", Proc. Natl. Acad. Sci., 85: 2444-2448, 1988; and D. J. Lipman and W. R. Pearson's "Fast and Sensitive Protein Similarity Search", Science, 227: 1435-1441, 1989. For a description of the BLAST algorithm, please refer to S. Altschul, W. Gish, W. Miller, E. W. Myers and D. Lipman's "a basic alignment search tool", Molecule Journal of Biology, 215: 403-410, 1990.

Nucleic Acid, Vector, Host Cell, and Preparation Method

In another aspect, the present application further provides one or more isolated nucleic acid molecules. The one or more nucleic acid molecules can encode the antibody or its antigen-binding fragment of the present application. For example, each of the one or more nucleic acid molecules can encode either the intact antibody or its antigen-binding fragment, or a part thereof (e.g., one or more of HCDR1-3, LCDR1-3, VL, VH, light chain or heavy chain).

At least one of the nucleic acid molecules of the present application can be subject to codon optimization. For example, the codon optimization method can include, but is not limited to: eliminating rare codons, adjusting GC content, increasing mRNA stability, adjusting mRNA secondary structure, rationally designing joints and adjusting the start codon environment.

In the present application, the nucleic acid molecule can include one or more nucleotide sequences selected from the group consisting of SEQ ID NO: 14 and SEQ ID NO: 15. In certain cases, the nucleic acid molecule can encode the light chain of the antibody C6G12 of the present application. For example, the nucleic acid molecule can include a nucleotide sequence as shown in SEQ ID NO: 14. In certain cases, the nucleic acid molecule can encode the heavy chain of the antibody C6G12 of the present application. For example, the nucleic acid molecule can include a nucleotide sequence as shown in SEQ ID NO: 15.

The nucleic acid molecules of the present application can be isolated from each other, e.g., they can include nucleotide sequences encoding the antibody or its antigen-binding fragment of the present application or a part thereof, respectively. The nucleic acid molecule of the present application can also include simultaneously a plurality of nucleotide sequences encoding the antibody or its antigen-binding fragment of the present application or a part thereof.

In the present application, the nucleic acid molecule can be synthesized by conventional methods in the art. For example, it can be produced or synthesized by the following methods: (i) amplification in vitro, e.g., by polymerase chain reaction (PCR) amplification, (ii) cloning and recombination, (iii) purification, e.g., separation by restriction enzyme digestion and gel electrophoresis, or (iv) synthesis, e.g., chemical synthesis. In certain cases, the nucleic acid molecule can be prepared by a recombinant DNA technology.

In the present application, the nucleic acid encoding the antibody or its antigen-binding fragment can be prepared by various methods known in the art, including, but not limited to, overlapping PCR by using restrictive fragment operation or using synthetic oligonucleotide. See, e.g., Sambrook et al., Molecular Cloning, A Laboratory Manual, Cold Spring Harbor Laboratory Press, Cold Spring Harbor, N.Y., 1989; and Ausube et al. Current Protocols in Molecular Biology, Greene Publishing and Wiley-Interscience, New York N.Y., 1993.

In another aspect, the present application provides one or more vectors including the one or more nucleic acid molecules of the present application. Each vector can include one or more nucleic acid molecules. Moreover, the vector can further include other gene(s), e.g., a marker gene that allows the selection of the vector in an appropriate host cell and under appropriate conditions. Moreover, the vector can further include an expression control element that allows the coding region to be properly expressed in an appropriate host. Such control element is well known by persons skilled in the art, e.g., it can include promoter, ribosome binding site, enhancer and other control elements regulating the transcription of gene or translation of mRNA, and the like. The one or more nucleic acid molecules of the present application can be operatively linked to the expression control element.

The vector can include, e.g., plasmid, cosmid, virus, phage, or other vectors commonly used in, e.g., genetic engineering. For example, the vector is an expression vector. For example, the expression vector can be T-easy.

In another aspect, the present application provides a cell, and the cell can include the one or more nucleic acid molecules of the present application and/or the one or more vectors of the present application. For example, each cell can include one nucleic acid molecule or one vector of the present application. For example, each cell or each kind of cell can include a plurality of (e.g., two or more, e.g., two kinds or more kinds) nucleic acid molecules or vectors of the present application. For example, the vector of the present application can be introduced into cells, e.g., eukaryotic cells, such as cells from plants, fungi or yeast cells, etc. The vectors of the present application can be introduced into cells by methods known in the art, such as electroporation, lipofectine transfection, lipofectamin transfection, and the like. For example, the cell can be CHO-S.

In another aspect, the present application provides a method of preparing the antibody or its antigen-binding fragment. The method can include culturing the host cell of the present application under conditions that allow the antibody or its antigen-binding fragment to be expressed. For example, the method can include using an appropriate medium, an appropriate temperature, and culturing time, that are understood by persons of ordinary skills in the art.

In some cases, the method can further include the step of isolating and/or purifying the antibody or its antigen-binding fragment. For example, the antibody or its antigen-binding fragment of the present application can be purified and isolated by affinity chromatography using protein G-sepharose or protein A-sepharose, or by gel electrophoresis and/or high performance liquid chromatography. For example, the protein A affinity purification can also be used.

Immunoconjugate, Pharmaceutical Composition, Use

In another aspect, the present application provides an immunoconjugate including the antibody or its antigen-binding fragment.

For example, the immunoconjugate can include at least one additional agent selected from the group consisting of chemotherapeutic agents, radioactive elements, cell growth inhibitors and cytotoxic agents. In certain embodiments, the antibody or its antigen-binding fragment and the at least one additional agent in the immunoconjugate can be linked via a joint molecule. For example, the antibody or its antigen-binding fragment and the at least one additional agent in the immunoconjugate can be covalently linked to the joint molecule, respectively.

In the present application, the at least one additional agent can include maytansine (maytansine) or its derivative. For example, the maytansine derivative can include maytansine derivative DM1.

In another aspect, the present application provides a pharmaceutical composition including the antibody or its antigen-binding fragment, the immunoconjugate or the cell, and optionally pharmaceutically acceptable adjuvants.

The pharmaceutically acceptable adjuvants can include buffers, antioxidants, preservatives, low molecular weight polypeptides, proteins, hydrophilic polymers, amino acids, carbohydrates, chelating agents, counterions, metal complexes and/or nonionic surfactants, etc.

In the present application, the pharmaceutical composition can be formulated for oral administration, intravenous administration, intramuscular administration, in situ administration at the tumor site, inhalation, rectal administration, vaginal administration, transdermal administration or administration via subcutaneous depot.

The pharmaceutical composition can be used to inhibit the growth of a tumor (e.g., an AXL positive tumor). For example, the pharmaceutical composition of the present application can inhibit or delay the development or progress of a disease, reduce the tumor size (or even substantially eliminate the tumor), and/or alleviate and/or stabilize the disease state.

The pharmaceutical composition of the present application can include a therapeutically effective amount of the antibody or its antigen-binding fragment. The therapeutically effective amount is a dose required to prevent and/or treat (at least partly treat) a disease or disorder (e.g., cancer) and/or any complication thereof in a subject suffering from or having a developing risk of the disease or disorder.

In another aspect, the present application provides use of the antibody or its antigen-binding fragment or the immunoconjugate in manufacture of a drug for preventing or treating tumors.

In the present application, the tumor can include an AXL positive tumor. For example, the tumor can include a tumor selected from the group consisting of lung cancer, skin cancer, renal cancer, pancreatic cancer, hematological tumor, breast cancer, ovarian cancer, lymphoma and myeloma. Alternatively, e.g., the tumor can include a tumor selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma.

In another aspect, the present application provides an antibody or its antigen-binding fragment or the immunoconjugate for preventing or treating tumors.

In the present application, the tumor can include an AXL positive tumor. For example, the tumor can include a tumor selected from the group consisting of lung cancer, skin cancer, renal cancer, pancreatic cancer, hematological tumor, breast cancer, ovarian cancer, lymphoma and myeloma. Alternatively, e.g., the tumor can include a tumor selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma.

In another aspect, the present application provides a method of preventing or treating tumors in a subject in need thereof, including administering to the subject the antibody or its antigen-binding fragment, the immunoconjugate or the pharmaceutical composition.

In the present application, the tumor can include an AXL positive tumor. For example, the tumor can include a tumor selected from the group consisting of lung cancer, skin cancer, renal cancer, pancreatic cancer, hematological tumor, breast cancer, ovarian cancer, lymphoma and myeloma. Alternatively, e.g., the tumor can include a tumor selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma.

In another aspect, the present application provides an antibody or its antigen-binding fragment for diagnosis of a disease or condition associated with the expression of the AXL protein.

In the present application, the disease or condition associated with the expression of the AXL protein can be selected from the group consisting of Zika virus infection, systemic lupus erythematosus, elevation of blood pressure, proteinuria, thyroid cancer, stomach cancer, lung cancer, skin cancer, renal cancer, pancreatic cancer, hematological tumor (e.g., acute myeloblastic leukemia), breast cancer (e.g., ER positive breast cancer), ovarian cancer (e.g., type I and type II epithelial ovarian cancer), lymphoma and myeloma, or, can be selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma.

In another aspect, the present application provides use of the antibody or its antigen-binding fragment in manufacture of a diagnostic agent, wherein the diagnostic agent is used for diagnosing a disease or condition associated with the expression of the AXL protein.

In the present application, the diagnostic agent can be used alone, or in combination with instrument, device, apparatus, or system. During the process of disease prevention, diagnosis, treatment monitoring, prognosis observation, health evaluation and hereditary disease prediction, the diagnostic agent can be used for in vitro tests on human body samples (e.g., various body fluids, cells, tissue samples, etc.). The diagnostic agent can be selected from the group consisting of reagents, kits, calibrators and quality controls.

The in vitro detection method can be selected from the group consisting of Western Blot, ELISA and immunohistochemistry. For example, the agent can include an agent capable of measuring the expression of the AXL protein. For example, the agent can be selected from the group consisting of agents for implementation of Western Blot, agents for implementation of ELISA, and agents for implementation of immunohistochemistry.

In the present application, the disease or condition associated with the expression of the AXL protein can be selected from the group consisting of Zika virus infection, systemic lupus erythematosus, elevation of blood pressure, proteinuria, thyroid cancer, stomach cancer, lung cancer, skin cancer, renal cancer, pancreatic cancer, hematological tumor (e.g., acute myeloblastic leukemia), breast cancer (e.g., ER positive breast cancer), ovarian cancer (e.g., type I and type II epithelial ovarian cancer), lymphoma and myeloma, or, can be selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma.

In another aspect, the present application provides a method of diagnosing a disease or condition associated with the expression of the AXL protein in a subject, including: contacting a sample derived from the subject with the antibody or its antigen-binding fragment, and determining the presence and/or amount of a substance capable of specifically binding to the antibody or its antigen-binding fragment in the sample.

In the present application, the disease or condition associated with the expression of the AXL protein can be selected from the group consisting of Zika virus infection, systemic lupus erythematosus, elevation of blood pressure, proteinuria, thyroid cancer, stomach cancer, lung cancer, skin cancer, renal cancer, pancreatic cancer, hematological tumor (e.g., acute myeloblastic leukemia), breast cancer (e.g., ER positive breast cancer), ovarian cancer (e.g., type I and type II epithelial ovarian cancer), lymphoma and myeloma, or, can be selected from the group consisting of non-small cell lung cancer, cutaneous squamous cell carcinoma, renal clear cell adenocarcinoma, pancreatic cancer, erythroleukemia, acute T cell leukemia, breast cancer, ovarian cancer, lymphoma and myeloma.

Without intending to be limited by any theory, the following examples are only for the purpose of illustrating the working modes of the device, method and system of the present application, and not used for limiting the scope of the present application invention.

EXAMPLES

Example 1. Preparation of Monoclonal Antibody by Hybridoma

Balb/c mice (Beijing Weitong Lihua Laboratory Animal Technology Co., Ltd.) were routinely immunized by a human AXL protein expressed by a mammalian cell—Chinese hamster ovary cell CHO-K1 (ATCC® CCL-61™) (a fusion protein of human AXL protein extracellular domain—human IgG1 Fc, named AXL-Fc, wherein for the sequence information of human AXL, refer to AAH32229.1; for the sequence of human IgG1 Fc fragments, refer to AEO21920.1; the amino acid sequence of the extracellular domain of the human AXL protein is as set forth in SEQ ID NO: 2; and the amino acid sequence of AXL-Fc is as set forth in SEQ ID NO: 3).

On Days 0, 14 and 28, in the presence of Freund's complete adjuvant (first injection) or Freund's incomplete adjuvant (second and third injections), Balb/c mice were subcutaneously injected with 100 μg of AXL-Fc. By using conventional hybridoma technology (Salhi et al., Biochem. J. 2004), spleen cells from mice were fused with mouse myeloma cells SP2/0 (ATCC). The cells were cultured in a plate containing HAT medium ($10^5$ cells per well) for hybridoma selection. After 12 days, the supernatant was harvested, and screened by direct enzyme-linked immunosorbent assay (ELISA) for clones with binding specificity to AXL (positive clones). The positives clones were subcloned by the limiting dilution method, and screened for the clone with the best specific binding activity, that was named 6G12.

The hybridoma cells corresponding to the positive clone 6G12 were amplified for large-scale in vitro production of antibodies. The supernatant was harvested and purified by protein G affinity chromatography, to obtain 6G12 antibodies for subsequent experiments.

The antibody gene in the monoclonal antibody cell strain was obtained by a conventional molecular biology method. According to Kabat analysis, the amino acid sequences of the LCDR1-3 of the 6G12 antibody are sequentially set forth in SEQ ID NO: 4, SEQ ID NO: 5 and SEQ ID NO: 6; the amino acid sequences of HCDR1-3 are sequentially set forth in SEQ ID NO: 7, SEQ ID NO: 8 and SEQ ID NO: 9; the amino acid sequence of the light chain variable region is set forth in SEQ ID NO: 10, and the amino acid sequence of the heavy chain variable region is set forth in SEQ ID NO: 11.

Example 2. The Monoclonal Antibody Recognizes the Antigen

The AXL-Fc prepared in Example 1 was coated on the ELISA plate at 1 μg/ml at 4° C. overnight. After washing with PBST, 10% fetal bovine serum was added and blocked at 37° C. for 1 hour. Different concentrations of the 6G12 antibodies were added and reacted at 37° C. for 1 hour. After washing with PBST, horseradish peroxidase-labeled goat anti-mouse secondary antibody (Goat Anti-mouse IgGHRP, Abcam) was added and reacted at 37° C. for 30 minutes. The plate was repeatedly washed with PBST for 5 times, and dried to remove residual droplets as possible by absorbent paper. 100 μl of TMB (eBioscience) was added into each well, and stood at room temperature (20±5▯) in the dark for 1.5 minutes. 100 μl of 2N $H_2SO_4$ stop solution was added to each well to stop the substrate reaction. The OD value was read with a microplate reader at 450 nm. The binding ability of the antibody to AXL-Fc was analyzed.

The results are shown in FIG. 1. The results show that the 6G12 antibody can specifically recognize the antigen AXL-Fc. The recognition activity is significantly dose-dependent, with an EC50 value of 669.3 ng/mL.

Example 3. Preparation of Chimeric Antibody

Figure 2:
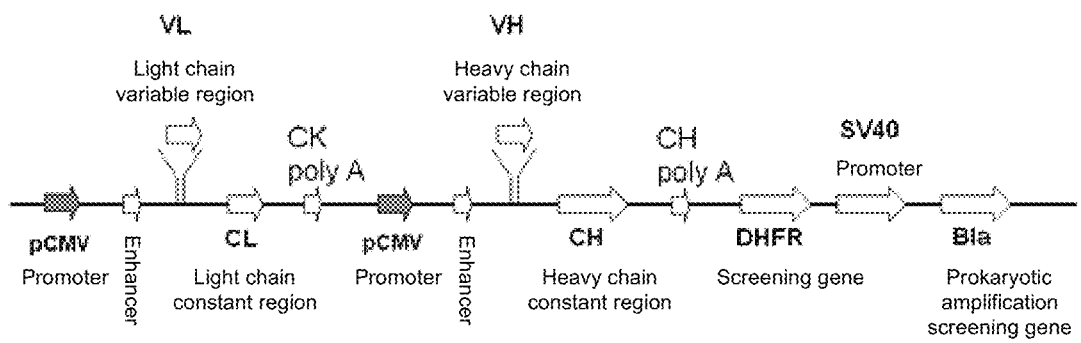
FIG. 2 shows the physical pattern of the vector constructed by the present application for preparing a chimeric antibody.

The obtained variable region gene of the 6G12 antibody was cloned into the eukaryotic expression vector pCMV-163 containing the human IgG1 constant region gene to construct the antibody expression vector. The physical map of the expression vector is shown in FIG. 2 (various components of the eukaryotic expression vector pCMV-163 are all known in the art, and are recombined in line with the order as shown). The chimeric antibody is called C6G12 (Chimeric 6G12) antibody. The above-mentioned antibody expression vector was transfected with ExpiCHO™ Expression System Kit (Thermo Fisher Scientific) into CHO-S cells for expression, and the cell culture supernatant containing the target protein (C6G12 antibody) was collected. By ELISA test, the goat anti-human IgG (Affinity Purified Antibody To Human IgG (H+L), KPL) and horseradish enzyme-labeled goat anti-human IgG (GOAT Anti human (HRP), Thermo Fisher Scientific) were subject to double sandwich ELISA for measuring the amount of C6G12 antibody in the supernatant (with the untransfected supernatant as a negative control and the pure human IgG as a standard). Sufficient supernatant was collected and subject to conventional Protein A affinity purification for the C6G12 antibody.

The amino acid sequence of the light chain of the C6G12 antibody is set forth in SEQ ID NO: 12, the nucleotide sequence of the light chain encoding the C6G12 antibody is set forth in SEQ ID NO: 14; the amino acid sequence of the heavy chain of the C6G12 antibody is set forth in SEQ ID NO 13, and the nucleotide sequence encoding the heavy chain of the C6G12 antibody is set forth in in SEQ ID NO: 15.

Example 4. Determination of Affinity of Chimeric Antibody

The antibody affinity was analyzed by BIACORE biomacromolecule interaction analyzer (GE Company). The anti-human IgG-Fc antibody (purchased from Abcam) was coupled to the chip, and used to capture the C6G12 antibody with an antibody concentration set as 0.5 μg/mL and an injection time of 60 seconds. AXL (Beijing Yiqiao Shenzhou Bio Technology Co., Ltd., 6×His label, with a molecular weight of 65 Kda) was taken as the mobile phase, with 6 concentration gradients (1, 0.4, 0.16, 0.064, 0.0256, 0.01024 μg/mL), a binding time of 180 seconds, and a dissociation time of 1200 seconds. The results of the affinity of the C6G12 antibody are shown in Table 1.

TABLE 1

| Determination of Affinity of C6G12 Antibody | | | |
|---|---|---|---|
| Antibody | Association Constant (1/Ms) | Dissociation Constant (1/s) | Dissociation Equilibrium Constant (M) |
| C6G12 | $2.614 \times 10^6$ | $4.023 \times 10^{-4}$ | $1.539 \times 10^{-10}$ |

Example 5. The Chimeric Antibody Binds to the Antigen

The AXL-Fc prepared in Example 1 was coated on the ELISA plate at 1 μg/ml at 4° C. overnight. After washing with PBST, 10% fetal bovine serum was added and blocked at 37° C. for 1 hour. Different concentrations of the C6G12 antibody prepared in Example 3 were added and reacted at 37° C. for 1 hour. After washing with PBST, horseradish peroxidase-labeled goat anti-human Fab secondary antibody (Goat Anti-human IgG(Fab')2 (HRP), Abcam) was added and reacted at 37° C. for 30 minutes. The plate was repeatedly washed with PBST for 5 times, and dried to remove residual droplets as possible by absorbent paper. 100 μl of TMB (eBioscience) was added to each well, and stood at room temperature (20±5° C.) in the dark for 1.5 minutes. 100 μl of 2N $H_2SO_4$ stop solution was added to each well to stop the substrate reaction. The OD value was read with a microplate reader at 450 nm. The binding ability of the C6G12 antibody to AXL-Fc was analyzed.

Figure 3:
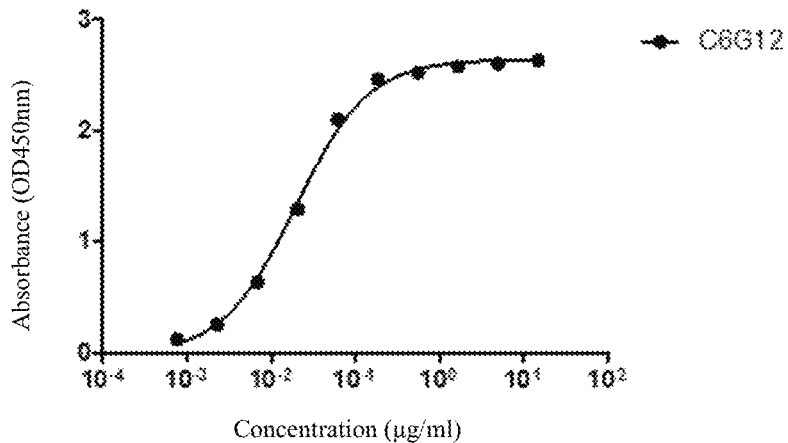
FIG. 3 shows the binding ability of the chimeric antibody of the present application specifically binding to AXL-Fc.

The results are shown in FIG. 3. The results show that the C6G12 antibody can recognize AXL-Fc; and the recognition activity is significantly dose-dependent, with an $EC_{50}$ value of 19.4 ng/mL.

Example 6. The Chimeric Antibody Specifically Recognizes the Antigen

Milk (Beijing Bomed Biotechnology Co., Ltd.), BSA (BOVOGEN), CD19 (Beijing Yiqiao Shenzhou Biotechnology Co., Ltd.), TROP2 (Beijing Yiqiao Shenzhou Biotechnology Co., Ltd.), BCMA (ACRO Biosystems), CD47 (Beijing Magpel Biotechnology Co., Ltd.), CD38 (Beijing Yiqiao Shenzhou Biotechnology Co., Ltd.), Gas6 (R&D) and each protein and AXL (ACRO Biosystems) were coated with ELISA plates at 1 μg/ml at 4° C. overnight, respectively. After washing with PBST, 10% fetal bovine serum was added and blocked at 37° C. for 1 hour. The C6G12 antibody prepared in Example 3 was added and reacted at 37° C. for 1 hour. After washing with PBST, horseradish peroxidase labeled goat anti-human IgG secondary antibody (GOAT Anti human (HRP), Thermo Fisher Scientific, #31412) was added and reacted at room temperature for 30 minutes. The plates were repeatedly washed with PBST for 5 times, and dried the residual droplets as possible on absorbent paper. 100 ml of TMB (eBioscience, #85-00-420) was added and stood at room temperature (20±50) in the dark for 1.5 minutes. 100 ml of 2N $H_2SO_4$ stop solution was added to each well to stop the substrate reaction. The OD value was read with a microplate reader at 450 nm. The binding abilities of antibodies and proteins were analyzed.

Figure 4:
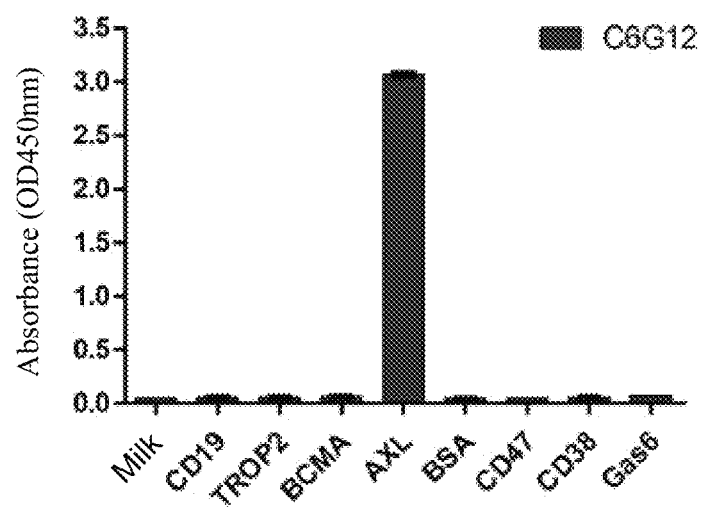
FIG. 4 shows the result of the chimeric antibody of the present application for specifically recognizing the antigen AXL.

The results are shown in FIG. 4. The results show that the C6G12 antibody can specifically recognize the target antigen AXL, but it has no significant binding reaction with milk, CD19, TROP2, BCMA, BSA, CD47, CD38, Gas6 and other proteins.

Example 7. The Chimeric Antibody Specifically Recognizes the Cell Surface Antigen The binding of the surface AXLs of a plurality of tumor cells including human non-small cell lung cancer A549 cells, renal clear cell adenocarcinoma 786-0 cells, human breast cancer MDA-MB-231 cells, human pancreatic cancer MIA PaCa-2 cells and other tumor cells (ATCC) to the C6G12 antibody was detected by use of flow cytometry. The logarithmic growth phase cells were collected, adjusted to a density of $5 \times 10^6$ cells/mL, and pre-cooled on ice. The C6G12 antibody was diluted to 20 g/ml with a pre-cooled normal saline containing 2% FBS. To 100 μl of cells was added an equal volume of the aforementioned diluted C6G12 antibody, and the mixture was reacted at 4° C. in the dark for 30 minutes. After the completion, the reaction mixture was washed twice with a pre-cooled normal saline containing 2% FBS (6000 rpm, 45 s). The secondary antibody PE Mouse Anti-Human IgG (BD Pharmingen) was diluted at a ratio of 1:5 with a pre-cooled normal saline containing 2% FBS. The cells were re-suspended in 100 μl of the diluted solution, and reacted at 4° C. in the dark for 30 min. After the reaction, the plate was washed twice with a pre-cooled normal saline containing 2% FBS (6000 rpm, 45 s). The cells were re-suspended in 400 l of 1% paraformaldehyde. The binding ability of the antibody to the cell surface antigen was analyzed by a flow cytometry (BD Calibur).

Figure 5A:
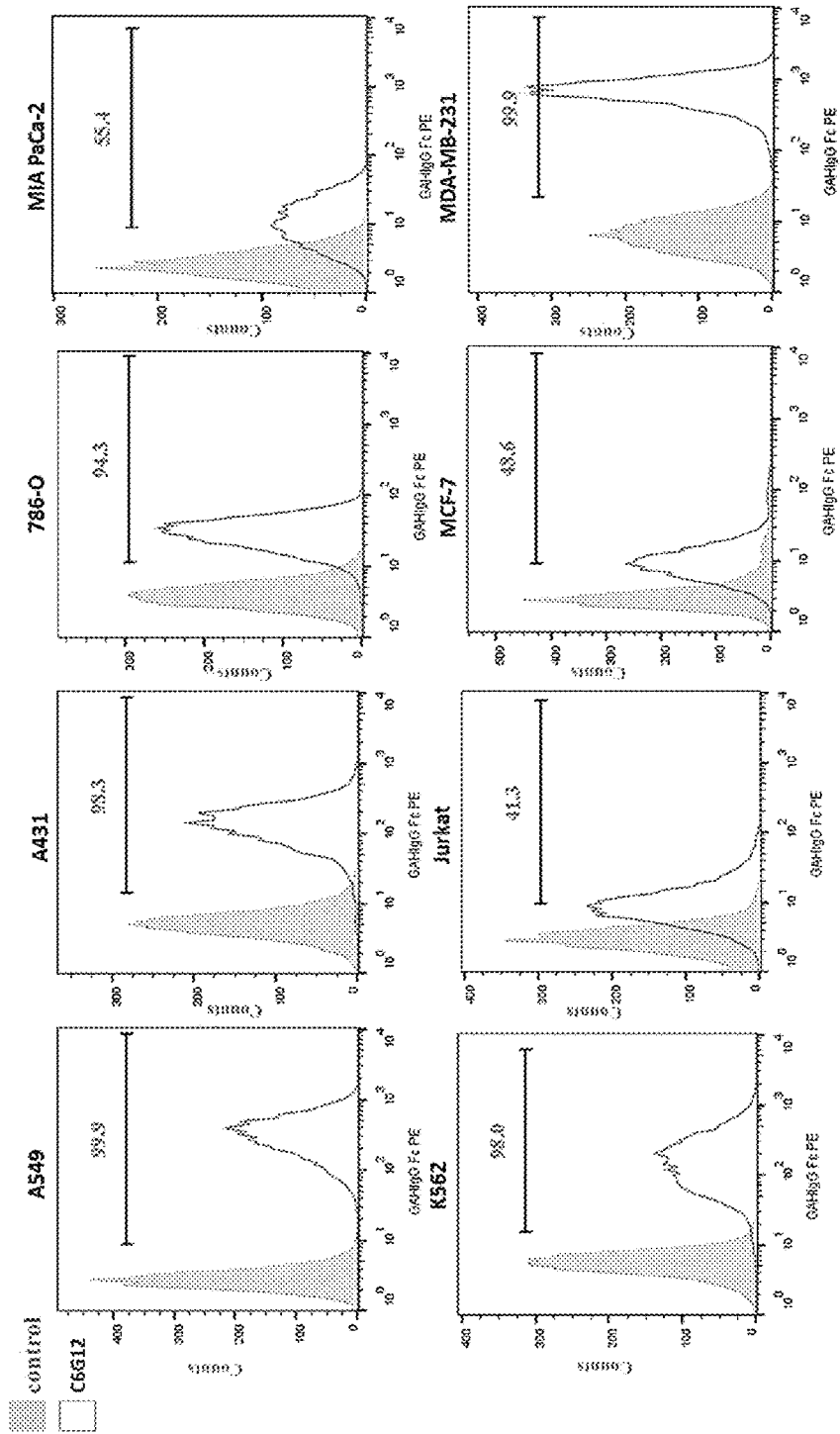
FIGS. 5A-5B show the result of the chimeric antibody of the present application for recognizing the tumor cell surface antigen AXL.
Figure 5B:
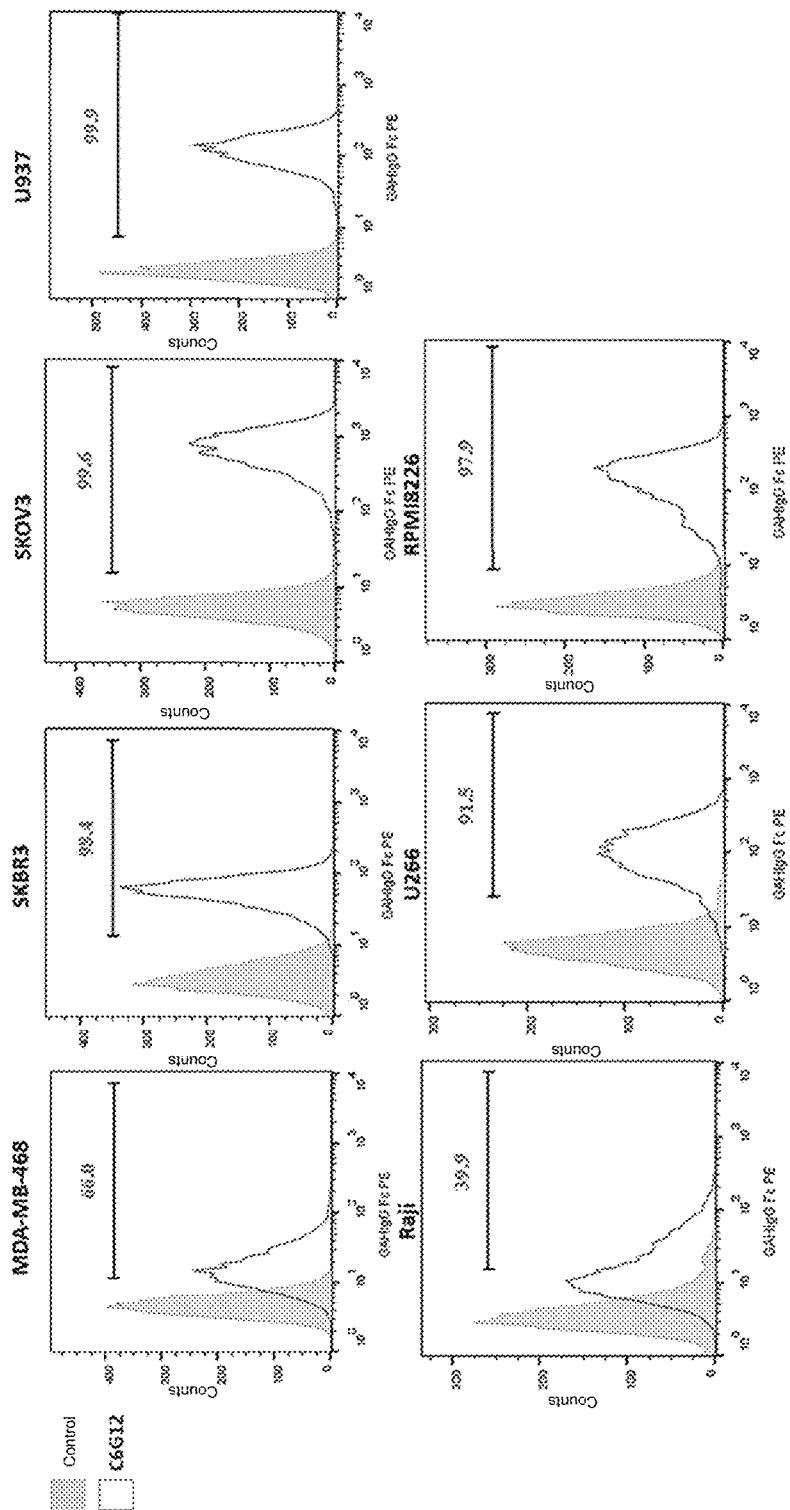

The results are shown in FIGS. 5A-5B. The results show that the C6G12 antibody can specifically recognize the surface AXL of human non-small cell lung cancer A549 cells, human skin squamous carcinoma A431 cells, renal clear cell adenocarcinoma 786-0 cells, human pancreatic cancer MIA PaCa-2 cells, erythroleukemia K562 cells, and acute T cell leukemia Jurkat cells, human breast cancer MCF-7 cells, human breast cancer MDA-MB-231 cells, human breast cancer MDA-MB-468 cells, human breast cancer SKBR3 cells, human ovarian cancer SKOV3 cells, lymphoma U-937 cells, lymphoma Raji cells, human myeloma U266 cells and human multiple myeloma RPMI8226 cells.

Example 8. Internalization Activity of Chimeric Antibody

The internalization efficiency of the C6G12 antibody on human non-small cell lung cancer A549 cells, renal clear cell adenocarcinoma 786-0 cells, human breast cancer MDA-MB-231 cells, and human pancreatic cancer MIA PaCa-2 cells were detected by flow cytometric technology. The logarithmic growth phase cells were collected, adjusted to a density of $5 \times 10^6$ cells/mL, and pre-cooled on ice. The C6G12 antibody was diluted to different concentrations with a pre-cooled normal saline containing 2% FBS. To 100 μl of cells was added an equal volume of the aforementioned diluted C6G12 antibody, and the mixture was incubated at 4° C. for 30 minutes. After the completion, the cells were washed for three times with a pre-cooled normal saline containing 2% FBS. The cells were placed at 4° C. or 37° C. for 2 hours and then washed twice. The secondary antibody PE Mouse Anti-Human IgG (BD Pharmingen) was diluted at 1:5 with a pre-cooled normal saline containing 2% FBS. The cells were resuspended in 100 μL of the diluted solution, and reacted at 4° C. in the dark for 30 minutes. After the reaction, the cells were washed for three times, and resuspended in 400 l of 1% paraformaldehyde. The fluorescence intensity on the surface of the cells cultured with the antibody at different temperatures was analyzed by flow cytometry (BD Calibur), and the internalization efficiency of the antibody was calculated according to the following equation.

Internalization efficiency=(Total surface MFI at 4° C.−Total surface MFI at 37° C.)/Total surface MFI at 4° C.×100%.

Figure 6:
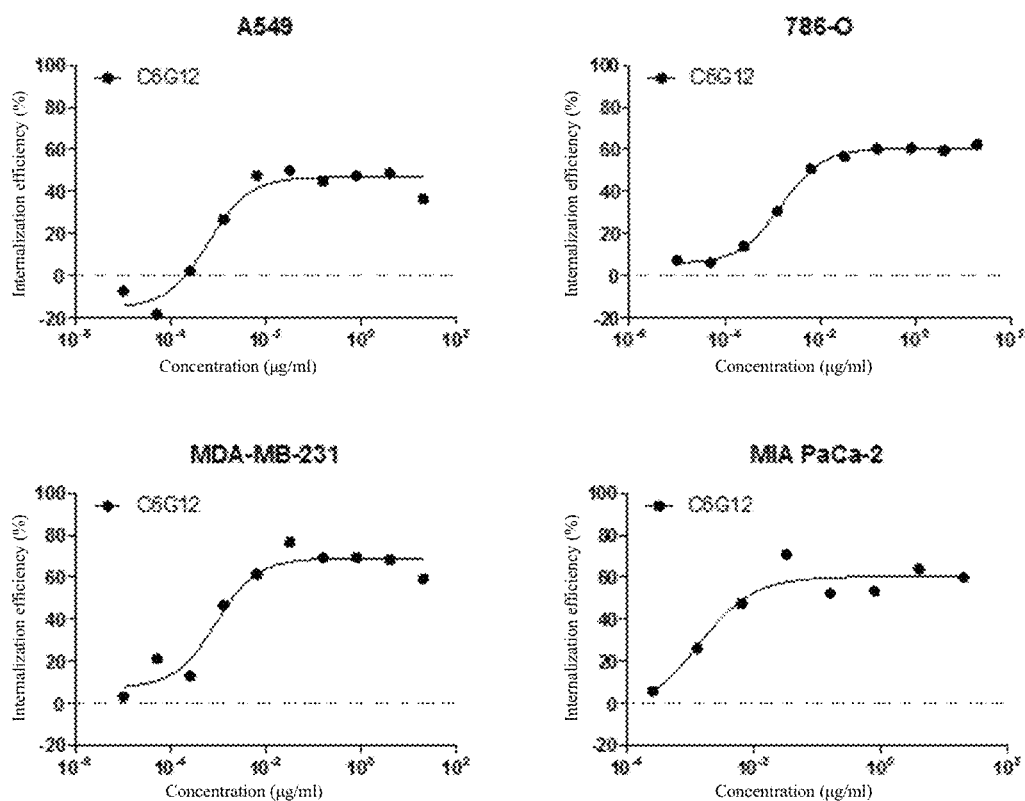
FIG. 6 shows the result of the internalization activity of the chimeric antibody of the present application to a tumor cell.

The results are shown in FIG. 6. The results showed that the C6G12 antibody can be effectively internalized on human non-small cell lung cancer A549 cells, renal clear cell adenocarcinoma 786-0 cells, human breast cancer MDA-MB-231 cells, and human pancreatic cancer MIA PaCa-2 cells. EC50 are 0.61 ng/mL, 1.5 ng/mL, 0.89 ng/mL, 1.3 ng/mL, respectively. It can be seen that the C6G12 antibody has good internalization activity.

Example 9. The Immunoconjugate Inhibits the Proliferation of Tumor Cells

MMC was used as the joint molecule in the immunoconjugate of the present application, and DM1 was used as the other agent in the immunoconjugate of the present application, to construct the immunoconjugate C6G12-MMC-DM1. The biological activity of the immunoconjugate C6G12-MMC-DM1 was evaluated, thereby further analyzing the potential of the C6G12 antibody to construct an immunoconjugate, such as, an antibody-small molecule drug conjugate (ADC) and the like.

A certain number of logarithmic growth phase cells (human non-small cell lung cancer A549 cells, renal clear cell adenocarcinoma 786-0 cells, human breast cancer MDA-MB-231 cells, human pancreatic cancer MIA PaCa-2 cells, erythroleukemia K562 cells) were inoculated into a 96-well plate. After 24 hours of adherent growth, different concentrations of drugs were added for 72 hours. After the drug effect was over, 10 μl of CCK-8 (Dojindo, Dojindo, Japan) was added to the culture plate per well, and incubated in a 37° C., 5% $CO_2$ incubator for 3-5 hours. The OD value was added with a microplate reader at a wavelength of 450 nm. The cell growth inhibition rate was calculated according to the following equation:

Inhibition rate=(the OD value of the control well−the OD value of the dosing well)/the OD value of the control well×100%

According to the inhibition rate of each concentration, the half inhibition concentration $IC_{50}$ was calculated.

Figure 7:
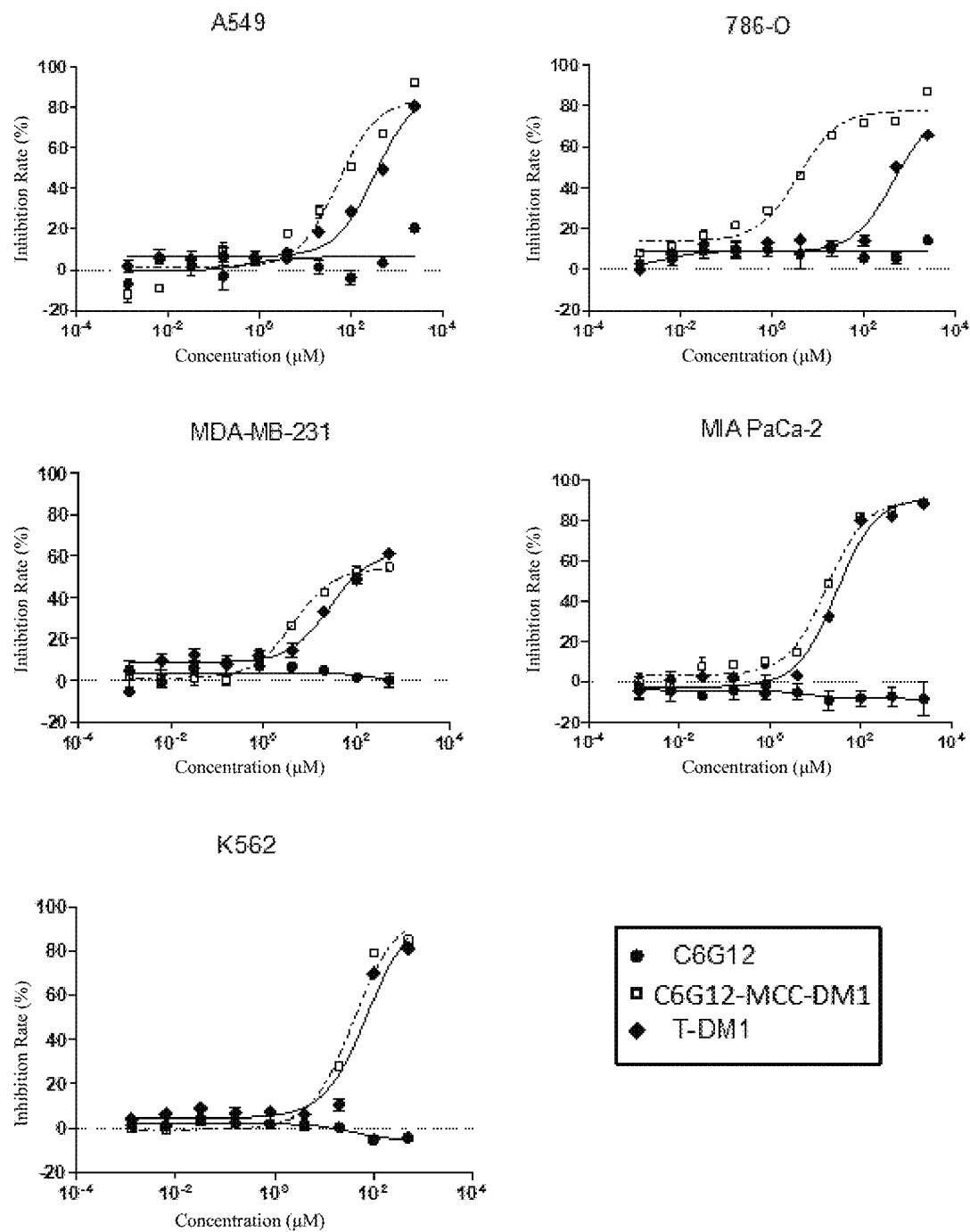
FIG. 7 shows the results of the immunoconjugate of the present application for inhibiting the proliferation of tumor cells.

The result is shown in FIG. 7. The results showed that the C6G12 antibody coupled with the maytansine derivative DM1 (C6G12-MCC-DM1) shows significant proliferation inhibition on a plurality of tumor cells (human non-small cell lung cancer A549 cells, renal clear cell adenocarcinoma 786-O cells, human breast cancer MDA-MB-231 cells, human pancreatic cancer MIA PaCa-2 cells, erythroleukemia K562 cells), with $IC_{50}$ of 52.27 μM, 3.74 μM, 4.35 μM, 18.1 μM and 39.36 μM, respectively. By using T-DM1 (Kadcyla™), the $IC_{50}$ of the above cells were 340.9 μM, 447.6 μM, 26.72 μM, 29.23 μM and 73.97 μM, respectively.

The foregoing detailed description is provided by way of explanation and example, and is not intended to limit the scope of the appended claims. Various changes of the embodiments listed herein are obvious to those of ordinary skills in the art, and are encompassed within the scope of the appended claims and their equivalents.

The invention claimed is:

1. An antibody or antigen-binding fragment thereof, which is capable of binding to an AXL protein, comprising a light chain variable region and a heavy chain variable region,
   said light chain variable region comprises LCDR1, LCDR2 and LCDR3,
   said LCDR1 comprises the amino acid sequence of SEQ ID NO:4;
   said LCDR2 comprises the amino acid sequence of SEQ ID NO:5;
   said LCDR3 comprises the amino acid sequence of SEQ ID NO:6;
   said heavy chain variable region comprises HCDR1, HCDR2 and HCDR3,
   said HCDR1 comprises the amino acid sequence of SEQ ID NO:7;
   said HCDR2 comprises the amino acid sequence of SEQ ID NO:8; and
   said HCDR3 comprises the amino acid sequence of SEQ ID NO:9.

2. The antibody or antigen-binding fragment thereof of claim 1, wherein said antibody is selected from the group consisting of: a monoclonal antibody, a single strand antibody, a chimeric antibody, a polyspecific antibody and a humanized antibody.

3. The antibody or antigen-binding fragment thereof of claim 1, wherein said antigen-binding fragment is selected from the group consisting of: Fab, Fab', F(ab)₂, F(ab')₂, Fv and ScFv fragments.

4. The antibody or antigen-binding fragment thereof of claim 1, wherein said antibody or antigen-binding fragment thereof comprises an antibody light chain or a fragment thereof, said antibody light chain or fragment thereof comprises a light chain variable region VL, wherein VL comprises the amino acid sequence of SEQ ID NO: 10.

5. The antibody or antigen-binding fragment thereof of claim 4, wherein said antibody light chain or fragment thereof comprises a human Igk constant region.

6. The antibody or antigen-binding fragment thereof of claim 4, wherein said antibody light chain or fragment thereof comprises the amino acid sequence of SEQ ID NO: 12.

7. The antibody or antigen-binding fragment thereof of claim 1, wherein said antibody or antigen-binding fragment thereof comprises an antibody heavy chain or a fragment thereof, said antibody heavy chain or fragment thereof comprises a heavy chain variable region VH, wherein VH comprises the amino acid sequence of SEQ ID NO: 11.

8. The antibody or antigen-binding fragment thereof of claim 7, wherein said antibody heavy chain or fragment thereof comprises a human IgG constant region.

9. The antibody or antigen-binding fragment thereof of claim 7, wherein said antibody heavy chain comprises the amino acid sequence of SEQ ID NO: 13.

10. An immunoconjugate comprising the antibody or antigen-binding fragment thereof of claim 1.

11. A pharmaceutical composition comprising the antibody or antigen-binding fragment thereof of claim 1, as well as optionally pharmaceutically acceptable adjuvants.

12. A method of treating a tumor in a subject in need thereof, said method comprising administering to said subject the antibody or antigen-binding fragment thereof of claim 1.

13. The method of claim 12, wherein said tumor comprises an AXL-positive tumor.

14. The method of claim 12, wherein said tumor is selected from the group consisting of: lung cancer, skin cancer, renal cancer, pancreatic cancer, hematological tumor, breast cancer, ovarian cancer, lymphoma and myeloma.

* * * * *

SEQUENCE LISTING

```
<160> NUMBER OF SEQ ID NOS: 15

<210> SEQ ID NO 1
<211> LENGTH: 894
<212> TYPE: PRT
<213> ORGANISM: Artificial Sequence
<220> FEATURE:
<223> OTHER INFORMATION: human AXL protein

<400> SEQUENCE: 1

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
```

```
                    245                 250                 255
His Cys Thr Leu Gln Ala Val Leu Ser Asp Gly Met Gly Ile Gln
                260                 265                 270
Ala Gly Glu Pro Asp Pro Glu Glu Pro Leu Thr Ser Gln Ala Ser
                275                 280                 285
Val Pro Pro His Gln Leu Arg Leu Gly Ser Leu His Pro His Thr Pro
    290                 295                 300
Tyr His Ile Arg Val Ala Cys Thr Ser Ser Gln Gly Pro Ser Ser Trp
305                 310                 315                 320
Thr His Trp Leu Pro Val Glu Thr Pro Glu Gly Val Pro Leu Gly Pro
                    325                 330                 335
Pro Glu Asn Ile Ser Ala Thr Arg Asn Gly Ser Gln Ala Phe Val His
                340                 345                 350
Trp Gln Glu Pro Arg Ala Pro Leu Gln Gly Thr Leu Leu Gly Tyr Arg
                355                 360                 365
Leu Ala Tyr Gln Gly Gln Asp Thr Pro Glu Val Leu Met Asp Ile Gly
            370                 375                 380
Leu Arg Gln Glu Val Thr Leu Glu Leu Gln Gly Asp Gly Ser Val Ser
385                 390                 395                 400
Asn Leu Thr Val Cys Val Ala Ala Tyr Thr Ala Ala Gly Asp Gly Pro
                    405                 410                 415
Trp Ser Leu Pro Val Pro Leu Glu Ala Trp Arg Pro Gly Gln Ala Gln
                420                 425                 430
Pro Val His Gln Leu Val Lys Glu Pro Ser Thr Pro Ala Phe Ser Trp
            435                 440                 445
Pro Trp Trp Tyr Val Leu Leu Gly Ala Val Val Ala Ala Ala Cys Val
        450                 455                 460
Leu Ile Leu Ala Leu Phe Leu Val His Arg Arg Lys Lys Glu Thr Arg
465                 470                 475                 480
Tyr Gly Glu Val Phe Glu Pro Thr Val Glu Arg Gly Glu Leu Val Val
                    485                 490                 495
Arg Tyr Arg Val Arg Lys Ser Tyr Ser Arg Arg Thr Thr Glu Ala Thr
                500                 505                 510
Leu Asn Ser Leu Gly Ile Ser Glu Glu Leu Lys Glu Lys Leu Arg Asp
            515                 520                 525
Val Met Val Asp Arg His Lys Val Ala Leu Gly Lys Thr Leu Gly Glu
        530                 535                 540
Gly Glu Phe Gly Ala Val Met Glu Gly Gln Leu Asn Gln Asp Asp Ser
545                 550                 555                 560
Ile Leu Lys Val Ala Val Lys Thr Met Lys Ile Ala Ile Cys Thr Arg
                    565                 570                 575
Ser Glu Leu Glu Asp Phe Leu Ser Glu Ala Val Cys Met Lys Glu Phe
                580                 585                 590
Asp His Pro Asn Val Met Arg Leu Ile Gly Val Cys Phe Gln Gly Ser
            595                 600                 605
Glu Arg Glu Ser Phe Pro Ala Pro Val Val Ile Leu Pro Phe Met Lys
        610                 615                 620
His Gly Asp Leu His Ser Phe Leu Leu Tyr Ser Arg Leu Gly Asp Gln
625                 630                 635                 640
Pro Val Tyr Leu Pro Thr Gln Met Leu Val Lys Phe Met Ala Asp Ile
                    645                 650                 655
Ala Ser Gly Met Glu Tyr Leu Ser Thr Lys Arg Phe Ile His Arg Asp
                660                 665                 670
```

```
Leu Ala Ala Arg Asn Cys Met Leu Asn Glu Asn Met Ser Val Cys Val
            675                 680                 685

Ala Asp Phe Gly Leu Ser Lys Lys Ile Tyr Asn Gly Asp Tyr Tyr Arg
        690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Arg Gly Asn Arg Leu
            755                 760                 765

Lys Gln Pro Ala Asp Cys Leu Asp Gly Leu Tyr Ala Leu Met Ser Arg
        770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
            820                 825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
        850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890
```

<210> SEQ ID NO 2
<211> LENGTH: 417
<212> TYPE: PRT
<213> ORGANISM: Artificial Sequence
<220> FEATURE:
<223> OTHER INFORMATION: human AXL protein extracellular domain

<400> SEQUENCE: 2

```
Ala Pro Arg Gly Thr Gln Ala Glu Glu Ser Pro Phe Val Gly Asn Pro
1               5                   10                  15

Gly Asn Ile Thr Gly Ala Arg Gly Leu Thr Gly Thr Leu Arg Cys Gln
            20                  25                  30

Leu Gln Val Gln Gly Glu Pro Pro Glu Val His Trp Leu Arg Asp Gly
        35                  40                  45

Gln Ile Leu Glu Leu Ala Asp Ser Thr Gln Thr Gln Val Pro Leu Gly
    50                  55                  60

Glu Asp Glu Gln Asp Asp Trp Ile Val Val Ser Gln Leu Arg Ile Thr
65                  70                  75                  80

Ser Leu Gln Leu Ser Asp Thr Gly Gln Tyr Gln Cys Leu Val Phe Leu
                85                  90                  95

Gly His Gln Thr Phe Val Ser Gln Pro Gly Tyr Val Gly Leu Glu Gly
            100                 105                 110

Leu Pro Tyr Phe Leu Glu Glu Pro Glu Asp Arg Thr Val Ala Ala Asn
        115                 120                 125

Thr Pro Phe Asn Leu Ser Cys Gln Ala Gln Gly Pro Pro Glu Pro Val
    130                 135                 140
```

```
Asp Leu Leu Trp Leu Gln Asp Ala Val Pro Leu Ala Thr Ala Pro Gly
145                 150                 155                 160

His Gly Pro Gln Arg Ser Leu His Val Pro Gly Leu Asn Lys Thr Ser
            165                 170                 175

Ser Phe Ser Cys Glu Ala His Asn Ala Lys Gly Val Thr Thr Ser Arg
        180                 185                 190

Thr Ala Thr Ile Thr Val Leu Pro Gln Gln Pro Arg Asn Leu His Leu
    195                 200                 205

Val Ser Arg Gln Pro Thr Glu Leu Glu Val Ala Trp Thr Pro Gly Leu
210                 215                 220

Ser Gly Ile Tyr Pro Leu Thr His Cys Thr Leu Gln Ala Val Leu Ser
225                 230                 235                 240

Asp Asp Gly Met Gly Ile Gln Ala Gly Glu Pro Asp Pro Pro Glu Glu
                245                 250                 255

Pro Leu Thr Ser Gln Ala Ser Val Pro Pro His Gln Leu Arg Leu Gly
            260                 265                 270

Ser Leu His Pro His Thr Pro Tyr His Ile Arg Val Ala Cys Thr Ser
    275                 280                 285

Ser Gln Gly Pro Ser Ser Trp Thr His Trp Leu Pro Val Glu Thr Pro
290                 295                 300

Glu Gly Val Pro Leu Gly Pro Pro Glu Asn Ile Ser Ala Thr Arg Asn
305                 310                 315                 320

Gly Ser Gln Ala Phe Val His Trp Gln Glu Pro Arg Ala Pro Leu Gln
                325                 330                 335

Gly Thr Leu Leu Gly Tyr Arg Leu Ala Tyr Gln Gly Gln Asp Thr Pro
            340                 345                 350

Glu Val Leu Met Asp Ile Gly Leu Arg Gln Glu Val Thr Leu Glu Leu
    355                 360                 365

Gln Gly Asp Gly Ser Val Ser Asn Leu Thr Val Cys Val Ala Ala Tyr
370                 375                 380

Thr Ala Ala Gly Asp Gly Pro Trp Ser Leu Pro Val Pro Leu Glu Ala
385                 390                 395                 400

Trp Arg Pro Gly Gln Ala Gln Pro Val His Gln Leu Val Lys Glu Pro
                405                 410                 415

Ser

<210> SEQ ID NO 3
<211> LENGTH: 650
<212> TYPE: PRT
<213> ORGANISM: Artificial Sequence
<220> FEATURE:
<223> OTHER INFORMATION: AXL-Fc

<400> SEQUENCE: 3

Ala Pro Arg Gly Thr Gln Ala Glu Glu Ser Pro Phe Val Gly Asn Pro
1               5                   10                  15

Gly Asn Ile Thr Gly Ala Arg Gly Leu Thr Gly Thr Leu Arg Cys Gln
            20                  25                  30

Leu Gln Val Gln Gly Glu Pro Pro Glu Val His Trp Leu Arg Asp Gly
        35                  40                  45

Gln Ile Leu Glu Leu Ala Asp Ser Thr Gln Thr Gln Val Pro Leu Gly
    50                  55                  60

Glu Asp Glu Gln Asp Asp Trp Ile Val Val Ser Gln Leu Arg Ile Thr
65                  70                  75                  80
```

-continued

```
Ser Leu Gln Leu Ser Asp Thr Gly Gln Tyr Gln Cys Leu Val Phe Leu
                85                  90                  95

Gly His Gln Thr Phe Val Ser Gln Pro Gly Tyr Val Gly Leu Glu Gly
            100                 105                 110

Leu Pro Tyr Phe Leu Glu Glu Pro Glu Asp Arg Thr Val Ala Ala Asn
            115                 120                 125

Thr Pro Phe Asn Leu Ser Cys Gln Ala Gln Gly Pro Pro Glu Pro Val
            130                 135                 140

Asp Leu Leu Trp Leu Gln Asp Ala Val Pro Leu Ala Thr Ala Pro Gly
145                 150                 155                 160

His Gly Pro Gln Arg Ser Leu His Val Pro Gly Leu Asn Lys Thr Ser
                165                 170                 175

Ser Phe Ser Cys Glu Ala His Asn Ala Lys Gly Val Thr Thr Ser Arg
            180                 185                 190

Thr Ala Thr Ile Thr Val Leu Pro Gln Gln Pro Arg Asn Leu His Leu
            195                 200                 205

Val Ser Arg Gln Pro Thr Glu Leu Glu Val Ala Trp Thr Pro Gly Leu
210                 215                 220

Ser Gly Ile Tyr Pro Leu Thr His Cys Thr Leu Gln Ala Val Leu Ser
225                 230                 235                 240

Asp Asp Gly Met Gly Ile Gln Ala Gly Glu Pro Asp Pro Pro Glu Glu
            245                 250                 255

Pro Leu Thr Ser Gln Ala Ser Val Pro Pro His Gln Leu Arg Leu Gly
            260                 265                 270

Ser Leu His Pro His Thr Pro Tyr His Ile Arg Val Ala Cys Thr Ser
            275                 280                 285

Ser Gln Gly Pro Ser Ser Trp Thr His Trp Leu Pro Val Glu Thr Pro
            290                 295                 300

Glu Gly Val Pro Leu Gly Pro Pro Glu Asn Ile Ser Ala Thr Arg Asn
305                 310                 315                 320

Gly Ser Gln Ala Phe Val His Trp Gln Glu Pro Arg Ala Pro Leu Gln
            325                 330                 335

Gly Thr Leu Leu Gly Tyr Arg Leu Ala Tyr Gln Gly Gln Asp Thr Pro
            340                 345                 350

Glu Val Leu Met Asp Ile Gly Leu Arg Gln Glu Val Thr Leu Glu Leu
            355                 360                 365

Gln Gly Asp Gly Ser Val Ser Asn Leu Thr Val Cys Val Ala Ala Tyr
            370                 375                 380

Thr Ala Ala Gly Asp Gly Pro Trp Ser Leu Pro Val Pro Leu Glu Ala
385                 390                 395                 400

Trp Arg Pro Gly Gln Ala Gln Pro Val His Gln Leu Val Lys Glu Pro
            405                 410                 415

Ser Leu Glu Pro Lys Ser Cys Asp Lys Thr His Thr Cys Pro Pro Cys
            420                 425                 430

Pro Ala Pro Glu Leu Leu Gly Gly Pro Ser Val Phe Leu Phe Pro Pro
            435                 440                 445

Lys Pro Lys Asp Thr Leu Met Ile Ser Arg Thr Pro Glu Val Thr Cys
450                 455                 460

Val Val Val Asp Val Ser His Glu Asp Pro Glu Val Lys Phe Asn Trp
465                 470                 475                 480

Tyr Val Asp Gly Val Glu Val His Asn Ala Lys Thr Lys Pro Arg Glu
            485                 490                 495

Glu Gln Tyr Asn Ser Thr Tyr Arg Val Val Ser Val Leu Thr Val Leu
```

```
                500              505                  510
His Gln Asp Trp Leu Asn Gly Lys Glu Tyr Lys Cys Lys Val Ser Asn
            515                  520              525

Lys Ala Leu Pro Ala Pro Ile Glu Lys Thr Ile Ser Lys Ala Lys Gly
            530                  535              540

Gln Pro Arg Glu Pro Gln Val Tyr Thr Leu Pro Pro Ser Arg Asp Glu
545                 550                  555              560

Leu Thr Lys Asn Gln Val Ser Leu Thr Cys Leu Val Lys Gly Phe Tyr
                565                  570              575

Pro Ser Asp Ile Ala Val Glu Trp Glu Ser Asn Gly Gln Pro Glu Asn
            580                  585              590

Asn Tyr Lys Thr Thr Pro Pro Val Leu Asp Ser Asp Gly Ser Phe Phe
            595                  600              605

Leu Tyr Ser Lys Leu Thr Val Asp Lys Ser Arg Trp Gln Gln Gly Asn
            610                  615              620

Val Phe Ser Cys Ser Val Met His Glu Ala Leu His Asn His Tyr Thr
625                 630                  635              640

Gln Lys Ser Leu Ser Leu Ser Pro Gly Lys
                645                  650

<210> SEQ ID NO 4
<211> LENGTH: 16
<212> TYPE: PRT
<213> ORGANISM: Artificial Sequence
<220> FEATURE:
<223> OTHER INFORMATION: LCDR1

<400> SEQUENCE: 4

Arg Ser Ser Arg Ser Leu Leu His Ser Asn Gly Phe Thr Tyr Leu Tyr
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: LCDR2

<400> SEQUENCE: 5

Gln Met Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3

<400> SEQUENCE: 6

Gly Gln Asn Leu Glu Leu Pro Leu Thr
1               5

<210> SEQ ID NO 7
<211> LENGTH: 6
<212> TYPE: PRT
<213> ORGANISM: Artificial Sequence
<220> FEATURE:
<223> OTHER INFORMATION: HCDR1

<400> SEQUENCE: 7

Ser Gly Tyr Tyr Trp Asn
```

```
<210> SEQ ID NO 8
<211> LENGTH: 16
<212> TYPE: PRT
<213> ORGANISM: Artificial Sequence
<220> FEATURE:
<223> OTHER INFORMATION: HCDR2

<400> SEQUENCE: 8

Tyr Arg Ser Tyr Asp Gly Ser Asn Asn Tyr Asn Pro Ser Leu Lys Asn
1               5                   10                  15

<210> SEQ ID NO 9
<211> LENGTH: 10
<212> TYPE: PRT
<213> ORGANISM: Artificial Sequence
<220> FEATURE:
<223> OTHER INFORMATION: HCDR3

<400> SEQUENCE: 9

Gly Trp Leu Leu His Tyr Thr Met Asp Tyr
1               5                   10

<210> SEQ ID NO 10
<211> LENGTH: 112
<212> TYPE: PRT
<213> ORGANISM: Artificial Sequence
<220> FEATURE:
<223> OTHER INFORMATION: VL

<400> SEQUENCE: 10

Glu Leu Val Met Thr Gln Ser Pro Phe Ser Asn Ala Val Thr Leu Gly
1               5                   10                  15

Thr Ser Ala Ser Ile Ser Cys Arg Ser Ser Arg Ser Leu Leu His Ser
                20                  25                  30

Asn Gly Phe Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Gly Gln Asn
                85                  90                  95

Leu Glu Leu Pro Leu Thr Phe Gly Ala Gly Thr Lys Leu Glu Leu Lys
            100                 105                 110

<210> SEQ ID NO 11
<211> LENGTH: 119
<212> TYPE: PRT
<213> ORGANISM: Artificial Sequence
<220> FEATURE:
<223> OTHER INFORMATION: VH

<400> SEQUENCE: 11

Gln Val Gln Leu Lys Gln Ser Gly Pro Gly Leu Val Lys Pro Ser Gln
1               5                   10                  15

Ser Leu Ser Leu Thr Cys Ser Val Thr Gly Phe Ser Ile Ser Ser Gly
                20                  25                  30

Tyr Tyr Trp Asn Trp Ile Arg Gln Phe Pro Gly Asn Lys Leu Glu Trp
        35                  40                  45

Met Gly Tyr Arg Ser Tyr Asp Gly Ser Asn Asn Tyr Asn Pro Ser Leu
```

```
                    50                  55                  60
Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                    85                  90                  95

Ala Arg Gly Trp Leu Leu His Tyr Thr Met Asp Tyr Trp Gly Gln Gly
                    100                 105                 110

Thr Ser Val Thr Val Ser Ser
                    115
```

<210> SEQ ID NO 12
<211> LENGTH: 219
<212> TYPE: PRT
<213> ORGANISM: Artificial Sequence
<220> FEATURE:
<223> OTHER INFORMATION: C6G12 light chain amino acid sequence

<400> SEQUENCE: 12

```
Glu Leu Val Met Thr Gln Ser Pro Phe Ser Asn Ala Val Thr Leu Gly
 1               5                   10                  15

Thr Ser Ala Ser Ile Ser Cys Arg Ser Ser Arg Ser Leu Leu His Ser
                    20                  25                  30

Asn Gly Phe Thr Tyr Leu Tyr Trp Tyr Leu Gln Lys Pro Gly Gln Ser
                    35                  40                  45

Pro Gln Leu Leu Ile Tyr Gln Met Ser Asn Leu Ala Ser Gly Val Pro
                    50                  55                  60

Asp Arg Phe Ser Ser Ser Gly Ser Gly Thr Asp Phe Thr Leu Arg Ile
 65                  70                  75                  80

Ser Arg Val Glu Ala Glu Asp Val Gly Val Tyr Tyr Cys Gly Gln Asn
                    85                  90                  95

Leu Glu Leu Pro Leu Thr Phe Gly Ala Gly Thr Lys Leu Glu Leu Lys
                    100                 105                 110

Arg Thr Val Ala Ala Pro Ser Val Phe Ile Phe Pro Pro Ser Asp Glu
                    115                 120                 125

Gln Leu Lys Ser Gly Thr Ala Ser Val Val Cys Leu Leu Asn Asn Phe
                    130                 135                 140

Tyr Pro Arg Glu Ala Lys Val Gln Trp Lys Val Asp Asn Ala Leu Gln
145                  150                 155                 160

Ser Gly Asn Ser Gln Glu Ser Val Thr Glu Gln Asp Ser Lys Asp Ser
                    165                 170                 175

Thr Tyr Ser Leu Ser Ser Thr Leu Thr Leu Ser Lys Ala Asp Tyr Glu
                    180                 185                 190

Lys His Lys Val Tyr Ala Cys Glu Val Thr His Gln Gly Leu Ser Ser
                    195                 200                 205

Pro Val Thr Lys Ser Phe Asn Arg Gly Glu Cys
                    210                 215
```

<210> SEQ ID NO 13
<211> LENGTH: 449
<212> TYPE: PRT
<213> ORGANISM: Artificial Sequence
<220> FEATURE:
<223> OTHER INFORMATION: C6G12 heavy chain amino acid sequence

<400> SEQUENCE: 13

```
Gln Val Gln Leu Lys Gln Ser Gly Pro Gly Leu Val Lys Pro Ser Gln
 1               5                   10                  15
```

-continued

Ser Leu Ser Leu Thr Cys Ser Val Thr Gly Phe Ser Ile Ser Ser Gly
            20                  25                  30

Tyr Tyr Trp Asn Trp Ile Arg Gln Phe Pro Gly Asn Lys Leu Glu Trp
            35                  40                  45

Met Gly Tyr Arg Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Gly Trp Leu Leu His Tyr Thr Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly

Lys

```
<210> SEQ ID NO 14
<211> LENGTH: 660
<212> TYPE: DNA
<213> ORGANISM: Artificial Sequence
<220> FEATURE:
<223> OTHER INFORMATION: C6G12 light chain nucleotide sequence

<400> SEQUENCE: 14
gagctcgtga tgacacagtc tccattctcc aatgcagtca ctcttggaac atcagcttcc      60
atctcctgca ggtctagtag gagtctccta catagtaatg gcttcactta tttgtattgg     120
tatctgcaga agccaggcca gtctcctcag ctcctgattt atcagatgtc aaccttgcc      180
tcaggagtcc cagacaggtt cagtagcagt gggtcaggaa ctgatttcac actgagaatc     240
agcagagtgg aggctgagga tgtgggtgtt tattactgtg tcaaaatct agagcttccg      300
ctcacgttcg gtgctgggac caagctggag ctgaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct caacagggg agagtgttag     660

<210> SEQ ID NO 15
<211> LENGTH: 1350
<212> TYPE: DNA
<213> ORGANISM: Artificial Sequence
<220> FEATURE:
<223> OTHER INFORMATION: C6G12 heavy chain nucleotide sequence

<400> SEQUENCE: 15
caggtgcagc tgaagcagtc aggacctggc ctcgtgaaac cttctcagtc tctgtctctc      60
acctgttctg tcactggctt ctccatcagc agtggttatt actggaactg gatccggcag     120
tttccaggaa acaaactgga atggatgggc tacagaagct acgacggttc aataactac      180
aacccatctc tcaaaaatcg aatctccatc actcgtgaca catctaagaa ccagttttc      240
ctgaagttga attctgtgac aactgaggac acagctacat attactgtgc aagaggatgg     300
ttactgcatt atactatgga ctactggggt caaggaacct cagtcaccgt ctcctcagct     360
agcaccaagg gcccatcggt cttccccctg gcaccctcct ccaagagcac ctctgggggc     420
acagcggccc tgggctgcct ggtcaaggac tacttcccg aaccggtgac ggtgtcgtgg      480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttccccc aaaacccaag gacaccctca tgatctcccg gacccctgag     780
gtcacgtgcg tggtggtgga cgtgagccac gaagaccccg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaac catctccaaa     1020
```

```
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                     1350
```